United States Patent
Adams et al.

(10) Patent No.: US 12,048,678 B2
(45) Date of Patent: Jul. 30, 2024

(54) COMPOUNDS FOR TREATING MYELIN RELATED DISORDERS

(71) Applicant: Case Western Reserve University, Cleveland, OH (US)

(72) Inventors: Drew Adams, Cleveland, OH (US); Paul J. Tesar, Wickliffe, OH (US); Dharmaraja Allimuthu, Cleveland, OH (US); Zita Hubler, Cleveland, OH (US); Fadi J. Najm, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 92 days.

(21) Appl. No.: 17/282,351

(22) PCT Filed: Oct. 1, 2019

(86) PCT No.: PCT/US2019/054011
§ 371 (c)(1),
(2) Date: Apr. 1, 2021

(87) PCT Pub. No.: WO2020/072456
PCT Pub. Date: Apr. 9, 2020

(65) Prior Publication Data
US 2021/0353642 A1    Nov. 18, 2021

Related U.S. Application Data

(60) Provisional application No. 62/740,186, filed on Oct. 2, 2018.

(51) Int. Cl.
| | |
|---|---|
| *A61K 31/165* | (2006.01) |
| *A61K 31/4453* | (2006.01) |
| *A61K 31/495* | (2006.01) |
| *A61K 31/54* | (2006.01) |
| *A61P 25/28* | (2006.01) |
| *A61K 31/395* | (2006.01) |
| *A61K 31/445* | (2006.01) |
| *A61K 31/55* | (2006.01) |

(52) U.S. Cl.
CPC ........ *A61K 31/165* (2013.01); *A61K 31/4453* (2013.01); *A61K 31/495* (2013.01); *A61K 31/54* (2013.01); *A61P 25/28* (2018.01); *A61K 31/445* (2013.01); *A61K 31/55* (2013.01); *A61K 31/5545* (2017.08)

(58) Field of Classification Search
CPC .... A61K 31/5545; A61K 31/165; A61P 25/28
See application file for complete search history.

(56) References Cited

U.S. PATENT DOCUMENTS

| | | | | |
|---|---|---|---|---|
| 2010/0074907 A1* | 3/2010 | Mi | ........................ | C07K 14/705 514/17.7 |
| 2012/0115852 A1* | 5/2012 | Schultz | ................... | A61P 35/02 544/360 |

FOREIGN PATENT DOCUMENTS

| | | |
|---|---|---|
| WO | 2008/077057 A2 | 6/2008 |
| WO | 2009/155209 A1 | 12/2009 |

OTHER PUBLICATIONS

National Center for Biotechnology Information. "PubChem Compound Summary for CID 73352232" PubChem, https://pubchem.ncbi.nlm.nih.gov/compound/73352232. Creation Date: Apr. 3, 2014. (Year: 2014).*
National Center for Biotechnology Information. "PubChem Compound Summary for CID 2177261, 1-(3,4-Dichloro-benzyl)-azocane" PubChem, https://pubchem.ncbi.nlm.nih.gov/compound/1-_3_4-Dichloro-benzyl_-azocane. Creation Date: Jul. 14, 2005. (Year: 2005).*
Norman et al. "Autotaxin inhibition: Development and application of computational tools to identify site-selective lead compounds." Bioorganic & Medicinal Chemistry (2013); vol. 21, Issue 17: 55448-5560. (Supplementary data. Supplementary Figures S1-S7 and Tables S1-S6.) (Year: 2013).*
Allimuthu et al., Diverse Chemical Scaffolds Enhance Oligodendrocyte Formation by Inhibiting CYP51, TM7SF2, or EBP. Cell Chem Biol. Apr. 18, 2019;26(4):593-599.
Hubler et al., Accumulation of 8,9-unsaturated sterols drives oligodendrocyte formation and remyelination. Nature. Aug. 2018;560(7718):372-376.
Invitation to Pay Additional Fees for Application No. PCT/US2019/054011, dated Jan. 16, 2020, 10 pages.

* cited by examiner

*Primary Examiner* — Jeffrey S Lundgren
*Assistant Examiner* — Chris E Simmons
(74) *Attorney, Agent, or Firm* — McCarter & English, LLP; Yu Lu

(57) ABSTRACT

Disclosed is a pharmaceutical composition comprising a compound represented by Structural Formula (I): or a pharmaceutically acceptable salt thereof, and a pharmaceutically acceptable carrier or diluent. Also disclosed is a method of treating a myelin related disorder in a subject, the method comprising administering to the subject an effective amount of a compound of Structural Formula (I) or a pharmaceutical composition comprising the compound of Structural Formula (I). The variables of Structural Formula (I) are described herein.

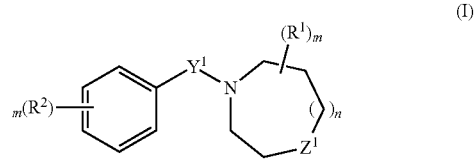

7 Claims, 7 Drawing Sheets

COMPOUNDS FOR TREATING MYELIN RELATED DISORDERS

CROSS-REFERENCE TO RELATED APPLICATIONS

This application is a U.S. national stage filing, under 35 U.S.C. § 371(c), of International Application No. PCT/US2019/054011, filed on Oct. 1, 2019, which claims priority to U.S. Provisional Application No. 62/740,186, filed on Oct. 2, 2018. The entire contents of each of the aforementioned applications are incorporated herein by reference.

BACKGROUND

Multiple sclerosis (MS) is a complex neurological disease characterized by deterioration of central nervous system (CNS) myelin. This insulating material, composed in its majority by lipids (70% lipids, 30% protein), protects axons and makes possible the saltatory conduction, which speeds axonal electric impulse. Demyelination of axons in chronic MS may result in axon degeneration and neuronal cell death, but more specifically, MS destroys oligodendrocytes, the highly specialized CNS cells that generate and maintain myelin.

Oligodendrocyte precursors (PDGFRα+, NG2-proteoglycan+), the immature oligodendrocytes, are generated in ventral areas of the developing brain from a common glial progenitor, actively migrate and proliferate populating the CNS to finally differentiate to premyelinating oligodendrocytes (O4+). At this maturation point, oligodendrocytes both target and extend myelin sheaths along axons or they die. Less explored has been however, the hypothesis of enhanced myelination and/or remyelination by either endogenous oligodendrocyte precursors or transplanted cells.

Inducing differentiation and/or promoting survival during the maturation of endogenous oligodendrocyte progenitors can stimulate and enhance the generation of new oligodendrocytes and intrinsic myelination and/or remyelination and treat diseases characterized by destruction or loss of myelin. Therefore, there is a need for compounds and therapeutic methods capable of enhancing the generation of new oligodendrocytes.

SUMMARY

Embodiments described herein generally relate to agents, compounds, compositions and methods for enhancing oligodendrocyte generation by inducing, promoting, and/or modulating oligodendrocyte precursor cell differentiation, proliferation and/or maturation as well as to methods for the treatment of disease or disorders in subjects where myelination or remyelination is beneficial to the subject.

In a first embodiment, the invention provides a pharmaceutical composition comprising a compound represented by Structural Formula (I):

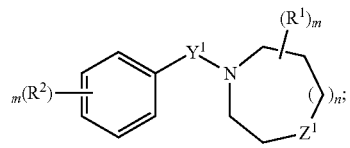

or a pharmaceutically acceptable salt thereof, and a pharmaceutically acceptable carrier or diluent, wherein $Y^1$ is a substituted or unsubstituted $C_1$-$C_6$ straight chain or branched alkylene;

$Z^1$ is $CR^1R^1$, $NR^3$ or O;

each $R^1$ and $R^2$ is independently selected from hydrogen, hydroxyl, substituted or unsubstituted alkyl, substituted or unsubstituted alkenyl, substituted or unsubstituted alkynyl, substituted or unsubstituted aryl, heteroaryl, heterocyclyl, substituted or unsubstituted aralkyl, biphenyl-$(CH_2)_p$—NH—$(CH_2)_r$, halo, —Si(alkyl)$_3$, sulfhydryl, alkoxy, alkenyloxy, alkynyloxy, aryloxy, acyl (including alkylcarbonyl (—CO-alkyl) and arylcarbonyl (—CO-aryl)), acyloxy (—O-acyl), alkoxycarbonyl (—(CO)—O-alkyl), aryloxycarbonyl (—(CO)—O-aryl), alkylcarbonato (—O—(CO)—O-alkyl), arylcarbonato (—O—(CO)—O-aryl), carboxy (—COOH), arylcarbamoyl (—(CO)—NH-aryl), —NR$^{10}$C(O)H, —C(O)NR$^{10}$R$^{10}$, —NR$^{10}$C(O)(alkyl), —C(S)NR$^{10}$R$^{10}$, —NR$^{10}$C(S)H, —NR$^{10}$C(S)(alkyl), carbamido (—NH—(CO)—NH$_2$), cyano(—CN), isocyano (—N$^+$C$^-$), cyanato (—O—CN), isocyanato (—O—N$^+$≡C$^-$), isothiocyanato (—S—CN), azido (—N=N$^+$=N$^-$), formyl (—(CO)—H), thioformyl (—(CS)—H), amino (—NH$_2$), alkyl amino, aryl amino, arylamido (—NH—(CO)-aryl), imino (—CR=NH where R is hydrogen, alkyl, aryl, alkary or aralkyl), alkylimino (—CR=N(alkyl), where R is hydrogen, alkyl, aryl, alkaryl or aralkyl), arylimino (—CR=N(aryl), where R=hydrogen, alkyl, aryl or alkaryl), nitro (—NO$_2$), nitroso (—NO), sulfo (—SO$_2$—OH), sulfonato (—SO$_2$—O$^-$), alkylsulfanyl (—S-alkyl; also termed "alkylthio"), arylsulfanyl (—S-aryl; also termed "arylthio"), alkylsulfinyl (—(SO)-alkyl), arylsulfinyl (—(SO)-aryl), alkylsulfonyl (—SO$_2$-alkyl), arylsulfonyl (—SO$_2$-aryl), sulfonamide (—SO$_2$—NH$_2$, —SO$_2$NY$_2$ (wherein Y is independently H, aryl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkylethers, phosphates and phosphate esters;

$R^3$ is selected from H, alkyl, phenyl (optionally substituted with halo, methoxy, halomethoxy, methyl, halomethyl, cyano), benzyl (optionally substituted with halo, methoxy, halomethoxy, methyl, halomethyl, cyano), hydroxyalkyl and alkoxyalkyl;

n is 1 or 2;

each m is independently 0, 1, 2, 3, 4 or 5;

p is 1, 2 3 or 4;

r is 1, 2, 3, 4, 5 or 6.

In another embodiment, the invention discloses a pharmaceutical composition comprising a compound represented by a structure of formula (II):

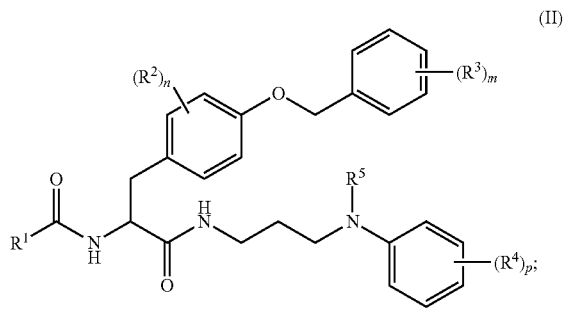

or a pharmaceutically acceptable salt thereof, and a pharmaceutically acceptable carrier or diluent, wherein:

$R^1$ is H, alkyl (optionally substituted with hydroxyl, alkoxy, thiol, alkylthiol, halo, cyano or phenyl optionally substituted with optionally substituted with halo, alkoxyl, haloalkoxy, alkyl, haloalkyl, cyano) or phenyl (optionally substituted with halo, alkoxyl, haloalkoxy, alkyl, haloalkyl, cyano), each $R^2$, $R^3$ and $R^4$ is independently optionally substituted with halo, alkoxyl, haloalkoxy, alkyl, haloalkyl or cyano;

$R^5$ is H or alkyl (preferably $C_1$-$C_3$ alkyl, more preferably $C_1$-$C_2$ alkyl);

m, n or p are independently 0, 1 or 2.

In one embodiment, the invention is a method of promoting re-myelination in a subject in need thereof, comprising administering to the subject an effective amount of a pharmaceutical composition described herein or a compound described herein or a pharmaceutically acceptable salt thereof.

In another embodiment, the invention is a method of treating a myelin related disorder in a subject, the method comprising administering to the subject an effective amount of a pharmaceutical composition described herein or a compound described herein or a pharmaceutically acceptable salt thereof.

Other features or advantages will be apparent from the following detailed description of several embodiments, and also from the appended claims.

BRIEF DESCRIPTION OF THE DRAWINGS

FIG. 4(a-g) illustrates data of a novel EBP inhibitor Compound 1 in promoting wrapping of MBP+ oligodendrocytes on microfibers and lacking the potent off-target effects of EBP inhibitors identified in repurposing screens.

DETAILED DESCRIPTION

Figures 1A, 1B:
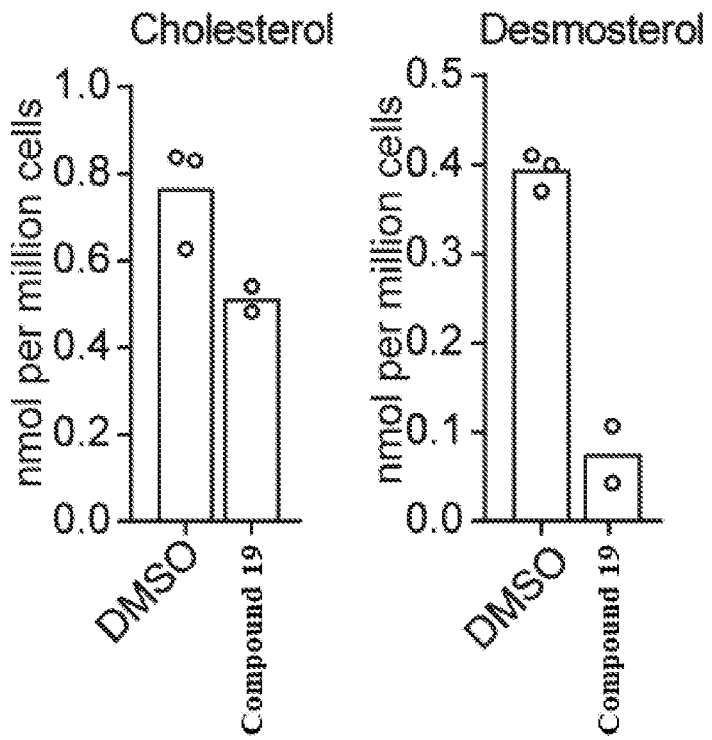
FIGS. 1a and 1b illustrate GC-MS-based quantification of cholesterol and desmosterol in OPCs after treatment with 10 μM of Compound 19.
Figure 1C:
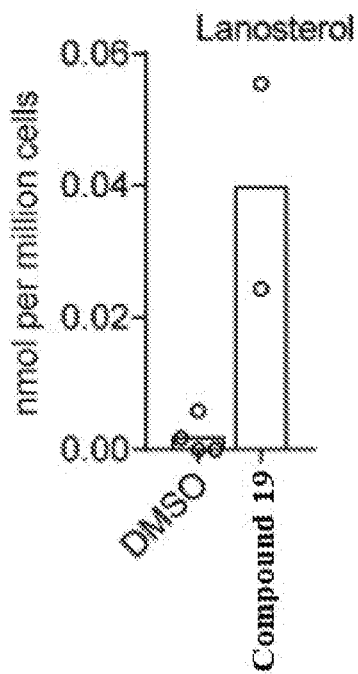
FIG. 1c illustrates GC-MS-based quantification of lanosterol after treatment with 10 μM of Compound 19.

Myelin is a lipid-rich membrane produced by mature oligodendrocytes that wraps around central nervous system (CNS) axons and enables saltatory conduction.[1] Multiple CNS diseases, including multiple sclerosis (MS) and genetic leukodystrophies, are characterized by the loss of myelin and oligodendrocytes.[2,3] Myelin loss can in some contexts be repaired via the differentiation of oligodendrocyte progenitor cells (OPCs) to new oligodendrocytes.[4,5] However, for diseases such as multiple sclerosis progress, the differentiation of OPCs becomes insufficient to repair the ongoing myelin loss.[3,5] Small molecules capable of enhancing oligodendrocyte formation can be useful to promote remyelination in a wide range of CNS diseases.

In a second embodiment, the invention provides a pharmaceutical composition comprising a compound of structural formula I or a pharmaceutically acceptable salt thereof, and a pharmaceutically acceptable carrier or diluent, wherein:

$Y^1$ is unsubstituted straight chain $C_1$-$C_6$ alkylene (preferably —$CH_2$—);

$Z^1$ is $CR^1R^1$, $NR^3$ or O;

each $R^1$ is independently selected from H, —OH, alkyl, alkenyl, alkynyl, hydroxyalkyl, thioalkoxy (—S-(alkyl)), alkoxy, alkoxyalkyl, —$NR^{10}C(O)H$, —$C(O)NR^{10}R^{10}$, —$NR^{10}C(O)(alkyl)$, —$C(S)NR^{10}R^{10}$, —$NR^{10}C(S)H$, —$NR^{10}C(S)(alkyl)$, —(CO)—O-alkyl, phenyl, (optionally substituted with halo, alkoxy, haloalkoxy, alkyl, haloalkyl, cyano), phenalkyl (optionally substituted with halo, alkoxy, haloalkoxy, alkyl, haloalkyl, cyano), wherein each alkyl, alkenyl, alkynyl, are optionally substituted with halo or hydroxyl;

each $R^2$ is independently selected from H, —OH, halo, alkyl, alkenyl, alkynyl, hydroxyalkyl, thioalkoxy, alkoxy, alkoxyalkyl, —$C(O)NR^{10}R^{10}$, —$NR^{10}R^{10}C(O)$—, —$C(S)NR^{10}R^{10}$, —$NR^{10}R^{10}C(S)$—, —(CO)—O-alkyl, phenyl (optionally substituted with halo, alkoxyl, haloalkoxy, alkyl, haloalkyl, cyano) or phenalkyl (optionally substituted with halo, alkoxyl, haloalkoxy, alkyl, haloalkyl, cyano), or

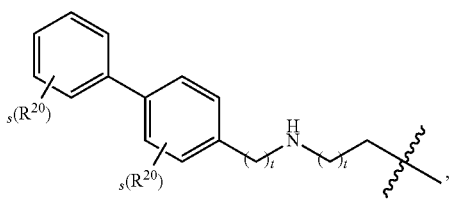

wherein each alkyl, alkenyl, alkynyl are optionally substituted with halo or hydroxyl;

$R^3$ is selected from H, alkyl, phenyl (optionally substituted with halo, methoxy, halomethoxy, methyl, halomethyl, cyano), benzyl (optionally substituted with halo, methoxy, halomethoxy, methyl, halomethyl, cyano), hydroxyalkyl, or alkoxyalkyl;

each $R^{10}$ is independently selected from H or alkyl;

each $R^{20}$ is independently selected from H, halo, alkoxy, haloalkoxy, alkyl, haloalkyl or cyano;

each m, s and t are independently 0, 1, 2 or 3.

In a third embodiment, the invention provides a pharmaceutical composition comprising a compound of structural formula I or a pharmaceutically acceptable salt thereof, and a pharmaceutically acceptable carrier or diluent, wherein:

$Y^1$ is unsubstituted $C_1$-$C_6$ straight chain alkylene (preferably —$CH_2$—);

$Z^1$ is $CR^1R^1$, $NR^3$ or O;

each $R^1$ is independently selected from H, OH, alkyl, hydroxyalkyl, phenyl (optionally substituted with halo, methoxy, halomethoxy, methyl, halomethyl, cyano), benzyl (optionally substituted with halo, methoxy, halomethoxy, methyl, halomethyl, cyano) or —C(O)NR$^{10}$R$^{10}$;

each $R^2$ is H, halo, $C_1$-$C_6$ alkyl, alkoxy, hydroxyl, hydroxyalkyl, thioalkoxy, phenyl (optionally substituted with halo, methoxy, halomethoxy, methyl, halomethyl, cyano), or

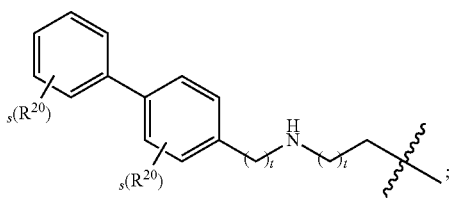

$R^3$ is selected from H, alkyl, phenyl (optionally substituted with halo, methoxy, halomethoxy, methyl, halomethyl, cyano), benzyl (optionally substituted with halo, methoxy, halomethoxy, methyl, halomethyl, cyano), hydroxyalkyl, or alkoxyalkyl;

each $R^{10}$ is independently selected from H or alkyl;

each $R^{20}$ is independently selected from H, alkoxy, haloalkoxy, methyl, halomethyl or cyano;

each m, s and t are independently 0, 1, 2 or 3.

In a fourth embodiment, the invention provides a pharmaceutical composition comprising a compound of structural formula (III):

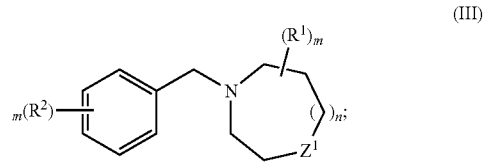

or a pharmaceutically acceptable salt thereof, and a pharmaceutically acceptable carrier or diluent; wherein:

each $R^1$ is independently selected from H, —OH, —$CH_2OH$—$CH_2CH_2OH$, —$CH_3$, —$CH_2CH_3$ or —C(O)NH$_2$;

each $R^2$ is independently selected from H, Cl, $C_1$-$C_4$ alkoxy, phenyl, methylthiol or

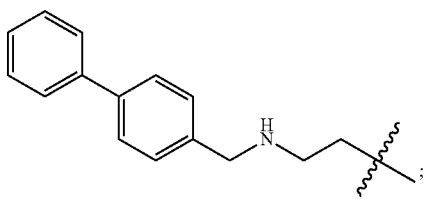 [SMILES: *CCNCc1ccc(-c2ccccc2)cc1]

$Z^1$ is $CR^1R^1$, $NR^3$, O;

$R^3$ is selected from H, methyl, ethyl, phenyl, benzyl, —$CH_2OH$, or —$CH_2CH_2OH$;

n is 1 or 2;

each m is independently 0, 1 or 2.

In a fifth embodiment, the invention provides a pharmaceutical composition comprising a compound represented by a structure selected from:

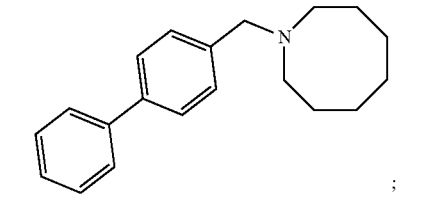

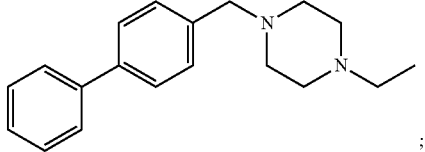

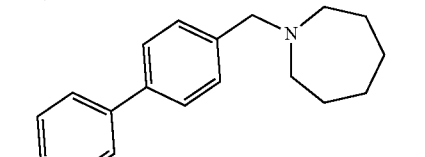

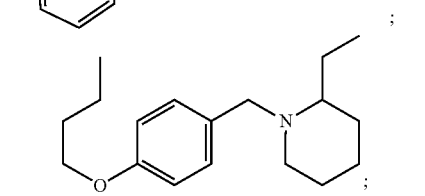

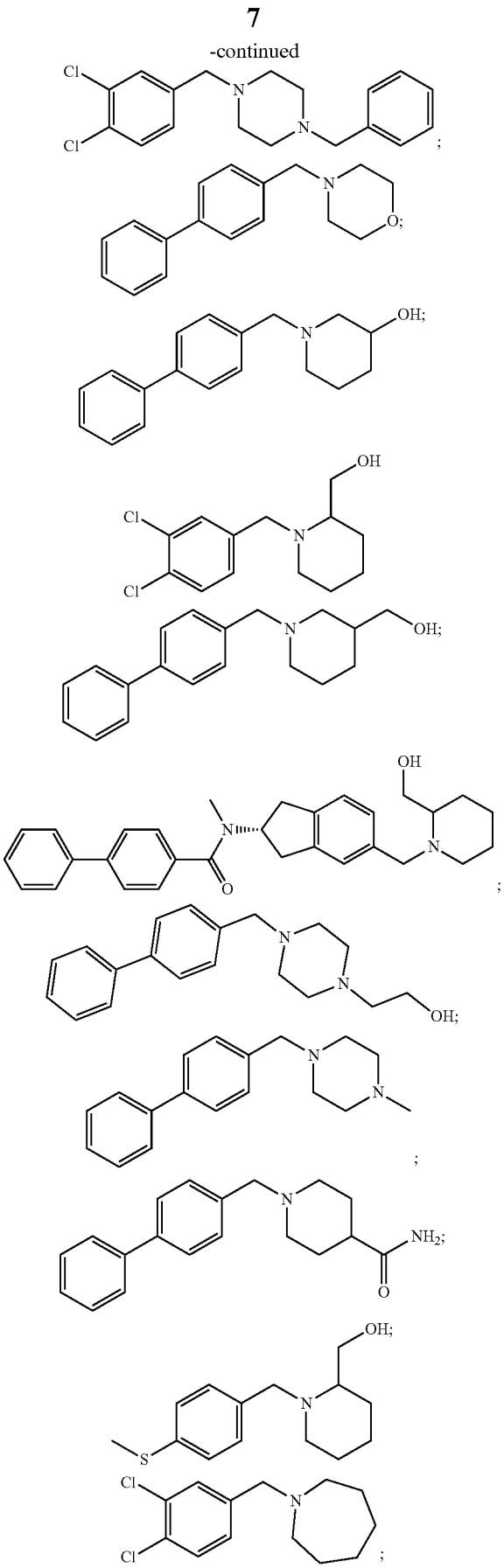

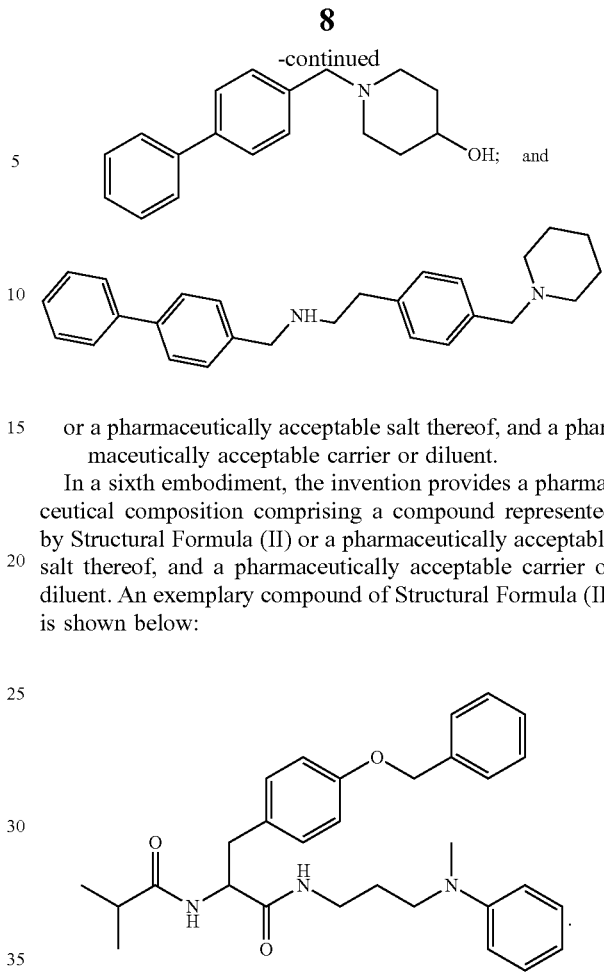

or a pharmaceutically acceptable salt thereof, and a pharmaceutically acceptable carrier or diluent.

In a sixth embodiment, the invention provides a pharmaceutical composition comprising a compound represented by Structural Formula (II) or a pharmaceutically acceptable salt thereof, and a pharmaceutically acceptable carrier or diluent. An exemplary compound of Structural Formula (II) is shown below:

Pharmaceutical compositions comprising this exemplary compound or a pharmaceutically salt thereof and a pharmaceutically acceptable carrier or diluent is encompassed within the invention.

For convenience, certain terms employed in the specification, examples, and appended claims are collected here. Unless defined otherwise, all technical and scientific terms used herein have the same meaning as commonly understood by one of ordinary skill in the art to which this application belongs.

Definitions

The term "alkyl" used alone or as part of a larger moiety, such as "alkoxy" or "haloalkyl"
and the like, means saturated aliphatic straight-chain or branched monovalent hydrocarbon radical. Unless otherwise specified, an alkyl group typically has 1-6 carbon atoms, i.e. $(C_1-C_6)$alkyl. As used herein, a "$(C_1-C_6)$alkyl" group means a radical having from 1 to 6 carbon atoms in a linear or branched arrangement. Examples include methyl, ethyl, n-propyl, iso-propyl, and the like.

An "alkylene group" is a saturated aliphatic branched or straight-chain divalent hydrocarbon radical. Unless otherwise specified, an alkylene group has 2-6 carbon atoms, e.g. $(C_2-C_6)$alkylene.

The term "alkenyl" used alone or as part of a larger moiety, such as "alkenyloxy" or "haloalkenyl" and the like, means branched or straight-chain monovalent hydrocarbon radical containing at least one double bond. Alkenyl may be mono or polyunsaturated, and may exist in the E or Z configuration. Unless otherwise specified, an alkenyl group typically has 2-6 carbon atoms, i.e., $(C_2-C_6)$alkenyl.

The term "alkynyl" used alone or as part of a larger moiety, such as "alkynyloxy" or "haloalkynyl" and the like, refers to a linear or branched hydrocarbon group of 2 to 6 carbon atoms containing at least one triple bond, such as ethynyl, n-propynyl, and the like.

The term "aryl", "aryl group" and "aryl ring" are used interchangeably and refer, alone or as part of a larger moiety as in "aryloxy" or "aralkyl", to a moncyclic or fused bicyclic carbocyclic aromatic group containing 6-10 carbon atoms. Examples of aryl groups include phenyl and naphthyl.

The terms "heteroaryl", "heteroaromatic", "heteroaryl ring", "heteroaryl group", "heteroaromatic ring", and "heteroaromatic group", are used interchangeably herein. "Heteroaryl" when used alone or as part of a larger moiety as in "heteroaralkyl" or "heteroarylalkoxy", refers to a monocyclic aromatic ring group having five to six ring atoms selected from carbon and at least one (typically 1 to 4, more typically 1 or 2) heteroatoms (e.g., oxygen, nitrogen or sulfur).

Examples of heteroaryls include but are not limited to furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), isothiazolyl, triazolyl (e.g., 2-triazolyl, 5-triazolyl), tetrazolyl (e.g., tetrazolyl), and thienyl (e.g., 2-thienyl, 3-thienyl).

"Heterocyclyl means a non-aromatic monocyclic group containing from 5-6 ring atoms wherein from 1-3 of the ring atoms are independently selected from N, NH, N(alkyl), NC(O)(alkyl), O, and S) and the remainder of the ring atoms are carbon. Examples of include, but are not limited to, azetidinyl, morpholinyl, thiomorpholinyl, pyrrolidinonyl, pyrrolidinyl, piperidinyl, piperazinyl, hydantoinyl, valerolactamyl, oxiranyl, oxetanyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, and tetrahydrothiopyranyl.

The terms "substituted" as in "substituted alkyl," "substituted aryl," "substituted alkenyl", "substituted alkynyl" and the like, as alluded to in some of the aforementioned definitions, is meant that in the alkyl, aryl, alkenyl, alkynyl or other moiety, at least one hydrogen atom bound to a carbon (or other) atom is replaced with one or more non-hydrogen substituents. Examples of such substituents include, without limitation: functional groups such as hydroxyl, substituted or unsubstituted alkyl, substituted or unsubstituted alkenyl, substituted or unsubstituted alkynyl, substituted or unsubstituted aryl, heteroaryl, heterocycloalkyl containing from 5-6 ring atoms (wherein from 1-3 of the ring atoms is independently selected from N, NH, N(alkyl), NC(O)(alkyl), O, and S), substituted or unsubstituted aralkyl, biphenyl-$(CH_2)_p$—NH—$(CH_2)_r$, halo, —Si(alkyl)$_3$, sulfhydryl, alkoxy, alkenyloxy, alkynyloxy, aryloxy, acyl (including alkylcarbonyl (—CO-alkyl) and arylcarbonyl (—CO-aryl)), acyloxy (—O-acyl), alkoxycarbonyl (—(CO)—O-alkyl), aryloxycarbonyl (—(CO)—O-aryl), alkylcarbonato (—O—(CO)—O-alkyl), arylcarbonato (—O—(CO)—O-aryl), carboxy (—COOH), arylcarbamoyl (—(CO)—NH-aryl), —NR$^{10}$C(O)H, —C(O)NR$^{10}$R$^{10}$, —NR$^{10}$C(O)(alkyl), —C(S)NR$^{10}$R$^{10}$, —NR$^{10}$C(S)H, —NR$^{10}$C(S)(alkyl), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), alkyl amino, aryl amino, arylamido (—NH—(CO)-aryl), imino (—CR=NH where R is hydrogen, alkyl, aryl, alkary or aralkyl), alkylimino (—CR=N(alkyl), where R is hydrogen, alkyl, aryl, alkaryl or aralkyl), arylimino (—CR=N(aryl), where R=hydrogen, alkyl, aryl or alkaryl), nitro (—NO$_2$), nitroso (—NO), sulfo (—SO$_2$—OH), sulfonato (—SO$_2$—O$^-$), alkylsulfanyl (—S-alkyl; also termed "alkylthio"), arylsulfanyl (—S-aryl; also termed "arylthio"), alkylsulfinyl (—(SO)-alkyl), arylsulfinyl (—(SO)-aryl), alkylsulfonyl (—SO$_2$-alkyl), arylsulfonyl (—SO$_2$-aryl), sulfonamide (—SO$_2$—NH$_2$, —SO$_2$NY$_2$ (wherein Y is independently H, aryl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkylethers, phosphates and phosphate esters, wherein R$^{10}$ is hydrogen or alkyl.

Compounds having a chiral center can exist as one of two enantiomers or as a mixture thereof. When a compound with a chiral center is named or depicted without indicating the stereochemistry of the chiral center, it is understood that the name or structure is meant to depict an enantiomerically-pure form, an enantiomerically-enriched form or the racemic form of the compound.

The term "geometric isomer" refers to cyclic compounds having at least two substituents, wherein the two substituents are both on the same side of the ring (cis) or wherein the substituents are each on opposite sides of the ring (trans). When a disclosed compound is named or depicted by structure without indicating stereochemistry, it is understood that the name or the structure encompasses one or more of the possible stereoisomers, or geometric isomers, or a mixture of the encompassed stereoisomers or geometric isomers.

The term "pharmaceutical composition" refers to a formulation containing the disclosed compounds in a form suitable for administration to a subject. The formulation comprises one or more compounds, or a pharmaceutically acceptable salt thereof, and a pharmaceutically acceptable carrier or diluent.

Pharmaceutically acceptable carrier" and "pharmaceutically acceptable diluent" refer to a substance that aids the formulation and/or administration of an active agent to and/or absorption by a subject and can be included in the compositions of the present disclosure without causing a significant adverse toxicological effect on the subject. Non-limiting examples of pharmaceutically acceptable carriers and/or diluents include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical excipients are suitable for use with disclosed compounds.

Methods of Treatment

The present invention provides a method of treating a neurodegenerative disease or disorder in a subject. In some embodiments, the neurodegenerative disease or disorder is a myelin related disorder. Myelin related diseases or disorders include diseases, disorders or injuries which relate to dysmyelination or demyelination in a subject's neural cells, e.g., CNS neurons.

The neurodegenerative disease contemplated for treatment by some aspects of the present invention can include a myelin related disorder. Myelin disorders can include any disease, condition (e.g., those occurring from traumatic spinal cord injury and cerebral infarction), or disorder related to demylination, insufficient myelination and remyelination, or dysmyelination in a subject. A myelin related disorder as used herein can arise from a myelination related disorder or demyelination resulting from a variety of neurotoxic insults. "Demyelination" as used herein, refers to the act of demyelinating, or the loss of the myelin sheath insulating the nerves, and is the hallmark of some neurodegenerative autoimmune diseases, including multiple sclerosis, transverse myelitis, chronic inflammatory demyelinating polyneuropathy, and Guillain-Barre Syndrome. Leukodystrophies are caused by inherited enzyme deficiencies, which cause abnormal formation, destruction, and/or abnormal turnover of myelin sheaths within the CNS white matter. Both acquired and inherited myelin disorders share a poor prognosis leading to major disability. Thus, some embodiments of the present invention can include methods for the treatment of neurodegenerative autoimmune diseases in a subject. Remyelination of neurons requires oligodendrocytes. The term "remyelination", as used herein, refers to the re-generation of the nerve's myelin sheath by replacing myelin producing cells or restoring their function.

Myelin related diseases or disorders which may be treated or ameliorated by the methods of the present invention include diseases, disorders or injuries which relate to dysmyelination or demyelination in a subject's brain cells, e.g., CNS neurons. Such diseases include, but are not limited to, diseases and disorders in which the myelin which surrounds the neuron is either absent, incomplete, not formed properly, or is deteriorating.

In one aspect, the present invention provides a method of treating a myelin related disease or disorder in a subject, the method comprising administering to the subject an effective amount of one or more disclosed compounds or a pharmaceutical composition disclosed herein or a pharmaceutically acceptable salt thereof.

Examples of myelin related diseases and disorders are multiple sclerosis (MS), neuromyelisits optica (NMO), progressive multifocal leukoencephalopathy (PML), encephalomyelitis (EPL), central pontine myelolysis (CPM), adrenoleukodystrophy, Alexander's disease, Pelizaeus Merzbacher disease (PMD), Vanishing White Matter Disease, Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, Bassen-Kornzweig syndrome, Marchiafava-Bignami syndrome, metachromatic leukodystrophy, trigeminal neuralgia, acute dissmeninated encephalitis, Guillian-Barre syndrome, Charcot-Marie-Tooth disease Bell's palsy, and mental health disorders such as schizophrenia.

One particular aspect of the present invention contemplates the treatment of multiple sclerosis in a subject. The method includes administering to the subject a therapeutically effective amount of one or more oligodendrocyte differentiation promoting compound(s) described above.

Multiple sclerosis (MS) is the most common demyelinating disease. In MS, the immune system attacks the protective sheath (myelin) that covers nerve fibers and causes communication problems between the brain and the rest of your body. Eventually, the disease can cause the nerves themselves to deteriorate or become permanently damaged. There are 4 disease courses that have been identified in multiple sclerosis: relapsing-remitting MS (RRMS), primary-progressive MS (PPMS), secondary-progressive MS (SPMS), and progressive-relapsing MS. Each course might be mild, moderate, or severe. It is contemplated that methods of the present invention can promote oligodendrocyte precursor cell differentiation in a subject, therefore leading to endogenous remyelination.

In some embodiments, the multiple sclerosis is relapsing remitting multiple sclerosis. In some additional embodiments, the multiple sclerosis is primary progressive multiple sclerosis. In a particular embodiment, the multiple sclerosis is secondary progressive multiple sclerosis.

In another aspect, the present invention provides a method of promoting myelination in a subject in need thereof, the method comprising administering to the subject an effective amount of one or more disclosed compounds disclosed herein or a pharmaceutically acceptable salt thereof or a pharmaceutical composition disclosed herein.

The terms "administer", "administering", "administration", and the like, as used herein, refer to methods that may be used to enable delivery of compositions to the desired site of biological action. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Administration techniques that can be employed with the agents and methods described herein are found in e.g., Goodman and Gilman, *The Pharmacological Basis of Therapeutics*, current ed.; Pergamon; and Remington's, *Pharmaceutical Sciences* (current edition), Mack Publishing Co., Easton, Pa. The compounds of the present invention may be administered, for example, by oral, parenteral, buccal, sublingual, nasal, patch, pump or transdermal administration and the pharmaceutical compositions formulated accordingly.

The term "effective amount" means an amount when administered to the subject which results in beneficial or desired results, including clinical results, e.g., inhibits, suppresses or reduces the symptoms of the condition being treated in the subject as compared to a control. Exemplary effective amounts include from 1 mg/kg per day to 500 mg/kg per day.

The term, "pharmaceutically acceptable salt" refers a salt that is pharmaceutically acceptable and that possesses the desired pharmacological activity of the parent compound. For example, the salt can be an acid addition salt. The pharmaceutically acceptable salts can be synthesized from a parent compound that contains a basic or acidic moiety by conventional chemical methods. Lists of salts are found in Remington's Pharmaceutical Sciences, 18th ed. (Mack Publishing Company, 1990). Compounds having basic groups can form pharmaceutically acceptable salts with pharmaceutically acceptable acid(s). Suitable pharmaceutically acceptable acid addition salts of the compounds described herein include salts of inorganic acids (such as hydrochloric acid, hydrobromic, phosphoric, metaphosphoric, nitric, and sulfuric acids) and of organic acids (such as acetic acid, benzenesulfonic, benzoic, ethanesulfonic, methanesulfonic, succinic, and trifluoroacetic acid acids). Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts).

A "patient," "subject," or "host" means either a human or non-human animal, such as a mammal. Thus, the subject of the herein disclosed methods can be a human, a non-human primate, horse, pig, rabbit, dog, sheep, goat, cow, cat, guinea pig or rodent. The term does not denote a particular age or sex.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

Embodiments described herein generally relate to agents, compounds, compositions and methods for enhancing oligodendrocyte generation by inducing, promoting, and/or modulating oligodendrocyte precursor cell differentiation, proliferation and/or maturation as well as to methods for the treatment of disease or disorders in subjects where myelination or remyelination is beneficial to the subject.

Myelin related diseases or disorders which may be treated or ameliorated by the methods of the present invention include a disease or disorder characterized by a myelin deficiency. Insufficient myelination in the central nervous system has been implicated in a wide array of neurological disorders. Among these are forms of cerebral palsy in which a congenital deficit in forebrain myelination in children with periventricular leukomalacia, contributes to neurological morbidity (Goldman et al., 2008) Goldman, S. A., Schanz, S., and Windrem, M. S. (2008). Stem cell-based strategies for treating pediatric disorders of myelin. Hum Mol Genet. 17, R76-83. At the other end of the age spectrum, myelin loss and ineffective repair may contribute to the decline in cognitive function associated with senescence (Kohama et al., 2011) Kohama, S. G., Rosene, D. L., and Sherman, L. S. (2011) Age (Dordr). Age-related changes in human and non-human primate white matter: from myelination disturbances to cognitive decline. Therefore, it is contemplated that effective compounds and methods of enhancing myelination and/or remyelination may have substantial therapeutic benefits in halting disease progression and restoring function in MS and in a wide array of neurological disorders.

In some embodiments, compounds described herein can be administered to a subject to promote myelination of CNS neurons in order to enhance cognition, which is known to be a myelin dependent process, in cognitive healthy subjects. In certain embodiments, compounds described herein can be administered in combination with cognitive enhancing (nootropic) agents. Exemplary agents include any drugs, supplements, or other substances that improve cognitive function, particularly executive functions, memory, creativity, or motivation, in healthy individuals. Non limiting examples include racetams (e.g., piracetam, oxiracetam, and anirac-etam), nutraceuticals (e.g., bacopa monnieri, *panax ginseng*, ginko *biloba*, and GABA), stimulants (e.g., amphetamine pharmaceuticals, methylphenidate, eugeroics, xanthines, and nicotine), L-Theanine, Tolcapone, Levodopa, Atomoxetine, and Desipramine.

EXEMPLIFICATION

Small Molecules

Multiple studies have used high-throughput chemical screening of bioactive libraries as a 'drug repurposing' approach to identify small molecules that enhance oligodendrocyte formation in vitro and promote functional remyelination in animal models of MS.[6-13] Recently, the inventors established that more than two dozen of these high-throughput screening hits share the ability to inhibit a narrow range of steps in cholesterol biosynthesis: sterol-C14-demethylase (CYP51), sterol-14-reductase (TM7SF2) and D8,7-sterol isomerase (EBP).[6] The cellular accumulation of the 8,9-unsaturated sterol substrates of these enzymes is a critical signaling node, since nine 8,9-unsaturated sterols promote oligodendrocyte formation when applied to OPCs in purified form.[6]

The inventors have now screened a diverse library of 10,000 small-molecules for enhancers of oligodendrocyte formation. In line with past repurposing screens, the inventors find that most leading hits inhibit either CYP51, TM7SF2, or EBP. Evaluation of the leading hits confirmed that potency for cellular inhibition of EBP correlated closely with potency for enhanced oligodendrocyte formation. Additionally, the inventors identified CW3388, a substantially more potent EBP inhibitor. In contrast to hits from past repurposing screens, these novel EBP inhibitors lack potent cellular targets beyond EBP.

Results

In contrast to repurposing efforts, phenotypic screening of diverse libraries has the potential to capture novel small molecules that enhance the formation of oligodendrocytes by a wide array of cellular mechanisms. The inventors screened an established assay measuring the differentiation of oligodendrocyte progenitor cells (OPCs) to mature, myelin basic protein-positive (MBP+) oligodendrocytes[7] against a library of 10,000 structurally-diverse small molecules at a uniform dose of 10 µM. From this library, potential hit molecules were selected for further evaluation on the basis of enhanced formation of MBP+ oligodendrocytes (see Methods for detailed hit-calling criteria). These putative hit molecules were then re-evaluated in two independent derivations of mouse epiblast stem cell-derived OPCs and also assayed for chemical purity, leading to a set of validated hits prioritized for further study.

As their recent work established inhibition of specific cholesterol pathway enzymes as the functional mechanism by which many small-molecules can enhance oligodendrocyte formation, the inventors next characterized the ability of our novel screening hits to inhibit cholesterol biosynthesis in OPCs at the screening dose. Gas chromatography/mass spectrometry (GC-MS) was used to quantitate levels of cholesterol and fourteen cholesterol pathway intermediates in OPCs. Interestingly, GC-MS analysis identified Compound 19 as causing inhibition of cholesterol biosynthesis (FIG. 1a). One molecule, Compound 19, led to accumulation of the 8,9-unsaturated sterol lanosterol, indicative of CYP51 inhibition (FIG. 1b).

These studies further establish that a large fraction of high-throughput screening hits that enhance oligodendrocyte formation inhibit CYP51 or EBP, in close agreement with past studies using repurposing libraries.

Next the validated hits were evaluated across a wide concentration range to determine their potency for enhancing oligodendrocyte formation. These studies revealed Compound 19, as a maximally potent enhancer of oligodendrocyte formation, with EC50 value in the mid-nanomolar range (Table 2). Compound 19 was initially characterized as inhibiting CYP51 in OPCs (FIG. 1b).

Mechanistically, it was previously established that oligodendrocyte formation is promoted by accumulation of 8,9-unsaturated sterols, whether induced by small molecule inhibition of CYP51, TM7SF2, or EBP or by supplying purified 8,9-unsaturated sterols directly to OPCs.[6]

Figure 2A:
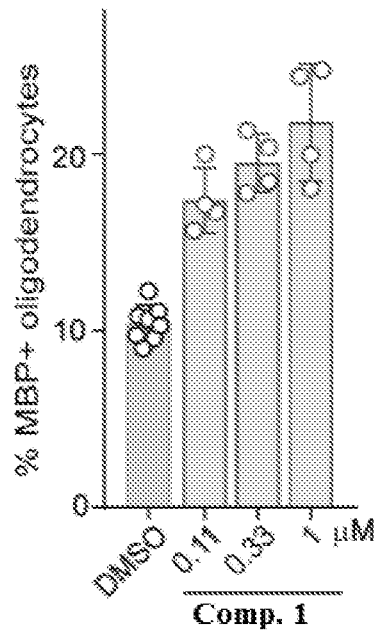
FIG. 2a illustrates Percentage of MBP+ oligodendrocytes generated from OPC-5 following treatment with Compound 1.
Figure 2B:
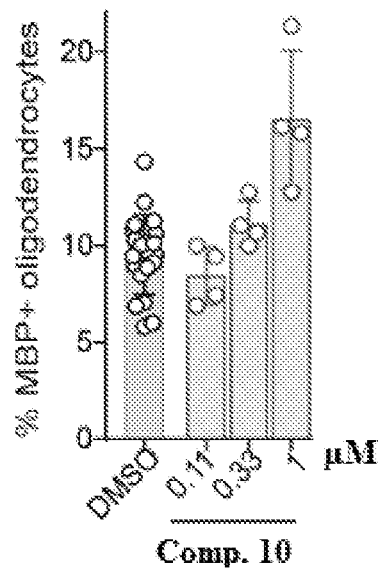
FIG. 2b illustrates Percentage of MBP+ oligodendrocytes generated from OPC-5 following treatment with Compound 10.
Figure 2C:
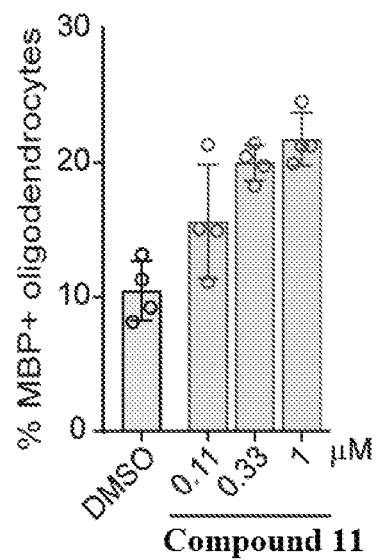
FIG. 2c illustrates Percentage of MBP+ oligodendrocytes generated from OPC-5 following treatment with Compound 11. n=4 wells per condition except DMSO, n=8.

Evaluation of a focused library of structural analogs of our previous lead molecules (Table 1) across a wide concentration range identified analogs whose ability to enhance oligodendrocyte formation was improved or diminished relative to the lead molecules (Table 2). The azacyclooctane-containing derivative Compound 1 showed optimal efficacy for enhancing oligodendrocyte formation among all analogs tested, with near maximal effects observed at 110 nM, the lowest dose tested (FIG. 2a). Compound 10 and Compound 11 also strongly promoted oligodendrocyte formation (FIGS. 2b and 2c).

TABLE 1

Compound Numbers and structures used in the evaluation study

| Compound No. | Compound Name | Structure |
|---|---|---|
| 1 | CW3388 | 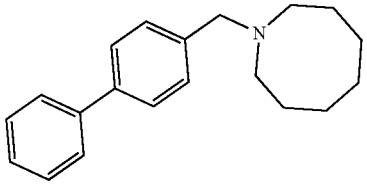 [SMILES: c1ccc(-c2ccc(CN3CCCCCCC3)cc2)cc1] |
| 2 | CW3343 | 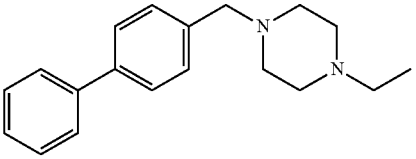 [SMILES: CCN1CCN(Cc2ccc(-c3ccccc3)cc2)CC1] |
| 3 | CW4133 | 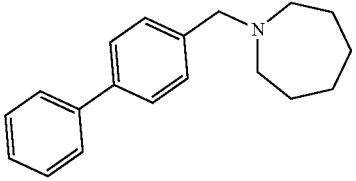 [SMILES: c1ccc(-c2ccc(CN3CCCCCC3)cc2)cc1] |
| 4 | CW2680 | 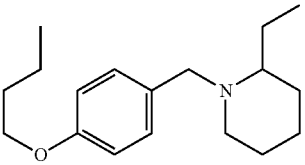 [SMILES: CCCCOc1ccc(CN2CCCCC2CC)cc1] |
| 5 | CW3657 | 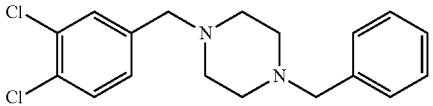 [SMILES: Clc1ccc(CN2CCN(Cc3ccccc3)CC2)cc1Cl] |
| 6 | CW2794 | 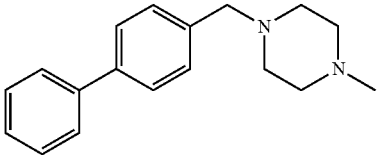 [SMILES: CN1CCN(Cc2ccc(-c3ccccc3)cc2)CC1] |
| 7 | CW3654 | 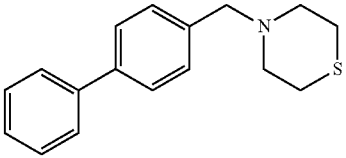 [SMILES: c1ccc(-c2ccc(CN3CCSCC3)cc2)cc1] |

TABLE 1-continued

Compound Numbers and structures used in the evaluation study

| Compound No. | Compound Name | Structure |
|---|---|---|
| 8 | CW2677 | 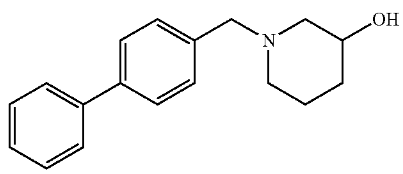 [SMILES: OC1CCCN(Cc2ccc(-c3ccccc3)cc2)C1] |
| 9 | CW8745 | 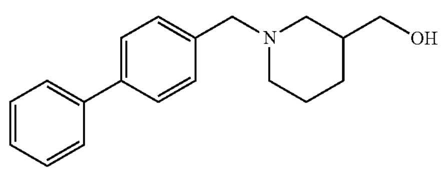 [SMILES: OCC1CCCN(Cc2ccc(-c3ccccc3)cc2)C1] |
| 10 | CW4644 | 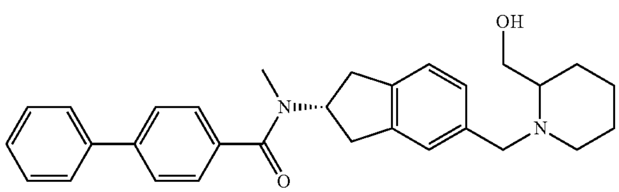 [SMILES: CN(C(=O)c1ccc(-c2ccccc2)cc1)[C@@H]1Cc2ccc(CN3CCCCC3CO)cc2C1] |
| 11 | CW1143 | 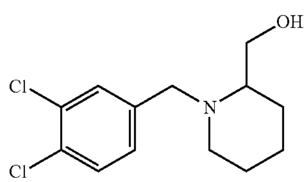 [SMILES: OCC1CCCCN1Cc1ccc(Cl)c(Cl)c1] |
| 12 | CW9326 | 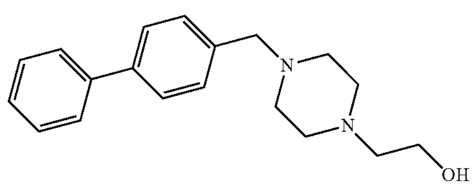 [SMILES: OCCN1CCN(Cc2ccc(-c3ccccc3)cc2)CC1] |
| 13 | CW2195 | 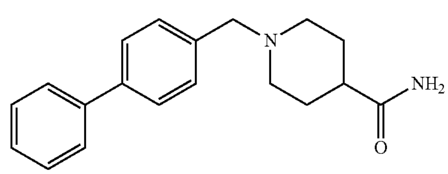 [SMILES: NC(=O)C1CCN(Cc2ccc(-c3ccccc3)cc2)CC1] |
| 14 | CW9306 | 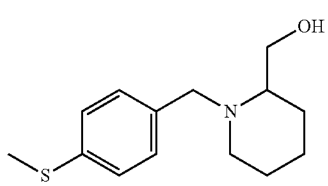 [SMILES: CSc1ccc(CN2CCCCC2CO)cc1] |
| 15 | CW2688 | 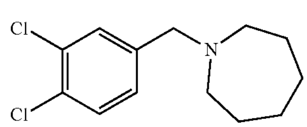 [SMILES: Clc1ccc(CN2CCCCCC2)cc1Cl] |

TABLE 1-continued

Compound Numbers and structures used in the evaluation study

| Compound No. | Compound Name | Structure |
|---|---|---|
| 16 | CW3169 | 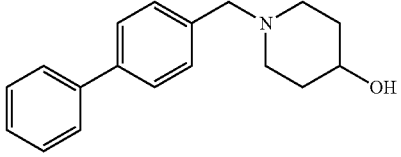 [SMILES: OC1CCN(Cc2ccc(-c3ccccc3)cc2)CC1] |
| 17 | CW2612 | 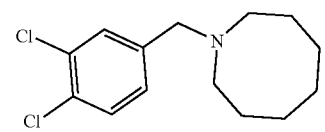 [SMILES: Clc1ccc(CN2CCCCCCC2)cc1Cl] |
| 18 | CW5420 | 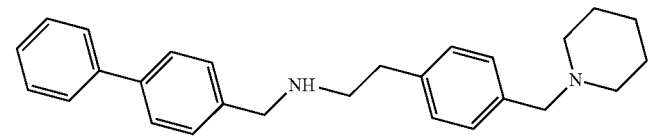 [SMILES: c1ccc(-c2ccc(CNCCc3ccc(CN4CCCCC4)cc3)cc2)cc1] |
| 19 | CW5020 | 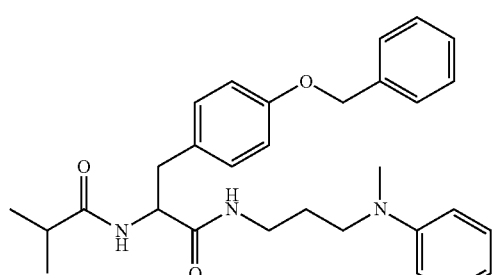 |

TABLE 2

Analogs representing the percentage of MBP+ oligodendrocytes generated after treatment with each small molecule for 72 h.

| Compound No. | % enhancement of MBP+ oligodendrocyte generation at 0.03 µM concentration | % enhancement of MBP+ oligodendrocyte generation at 0.1 µM concentration | % enhancement of MBP+ oligodendrocyte generation at 0.3 µM concentration | % enhancement of MBP+ oligodendrocyte generation at 1 µM concentration |
|---|---|---|---|---|
| 1 | B | D | D | D |
| 2 | B | C | D | D |
| 3 | B | B | C | D |
| 4 | A | B | A | B |
| 5 | A | B | C | C |
| 6 | A | B | C | C |
| 7 | A | C | B | C |
| 8 | B | B | C | C |
| 9 | B | B | C | C |
| 10 | B | C | D | D |
| 11 | B | C | D | D |
| 12 | A | B | C | D |
| 13 | B | B | C | D |
| 14 | B | C | C | C |
| 15 | A | B | C | C |
| 16 | B | B | B | C |

TABLE 2-continued

Analogs representing the percentage of MBP+ oligodendrocytes
generated after treatment with each small molecule for 72 h.

| Compound No. | % enhancement of MBP+ oligodendrocyte generation at 0.03 µM concentration | % enhancement of MBP+ oligodendrocyte generation at 0.1 µM concentration | % enhancement of MBP+ oligodendrocyte generation at 0.3 µM concentration | % enhancement of MBP+ oligodendrocyte generation at 1 µM concentration |
|---|---|---|---|---|
| 17 | A | A | A | A |
| 18 | B | B | B | C |
| 19 | B | B | C | C |

Enhancement of MBP+ oligodendrocyte generation:
A = 20% or less;
B = 20-30%;
C = 30-40%;
D = more than 40%

Figure 3A:
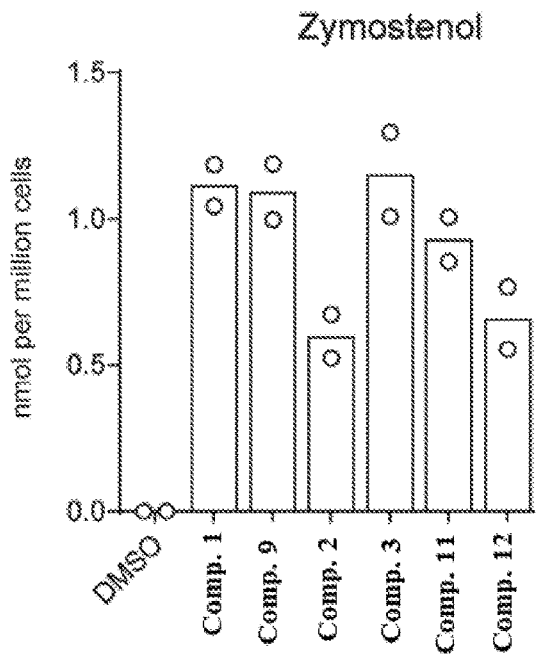
FIGS. 3a, 3b and 3c illustrate quantification of zymostenol, cholesterol and desmosterol in OPCs after treatment with indicated small molecule enhancers of oligodendrocyte formation using GC-MS.
Figure 3B:
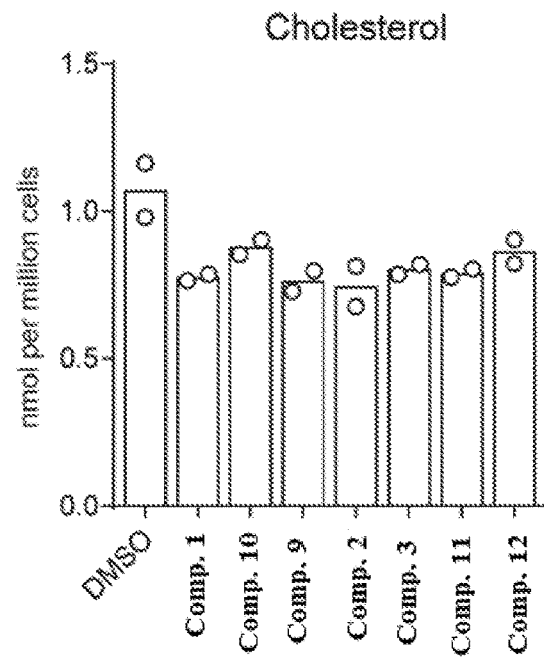
Figure 3C:
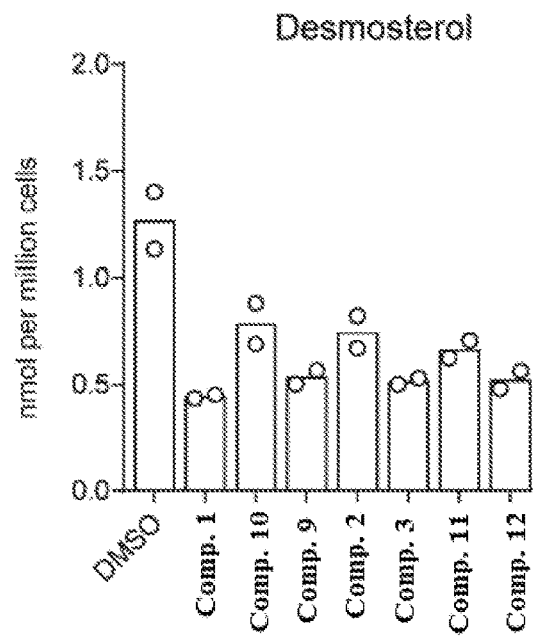
Figure 3D:
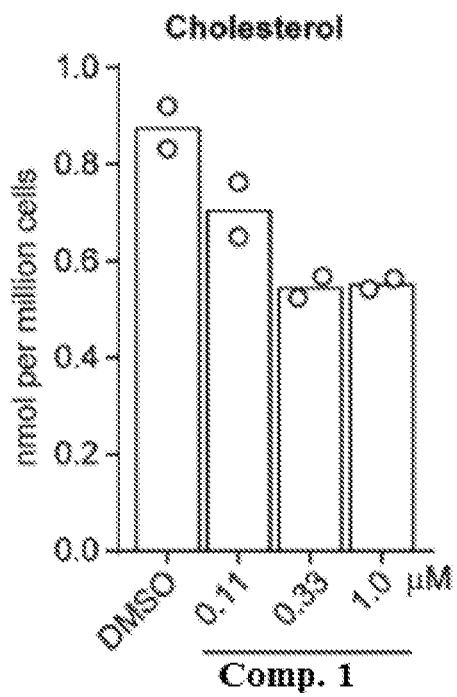
FIGS. 3d and 3e illustrates levels of cholesterol and desmosterol measured in OPCs after treatment with Compound 1 (at indicated doses) using GC-MS.
Figure 3E:
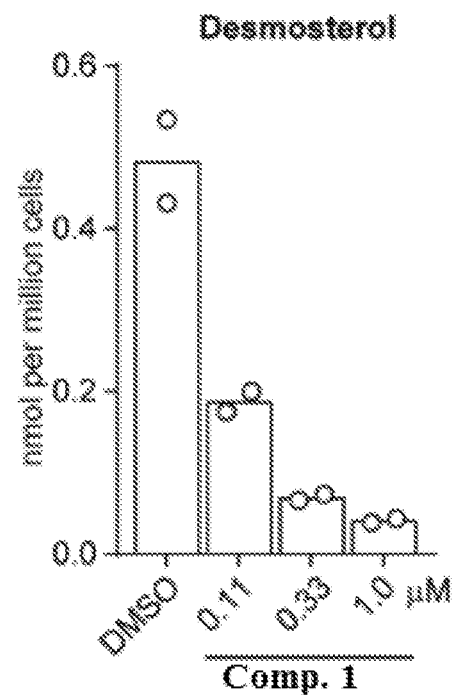
Figure 3F:
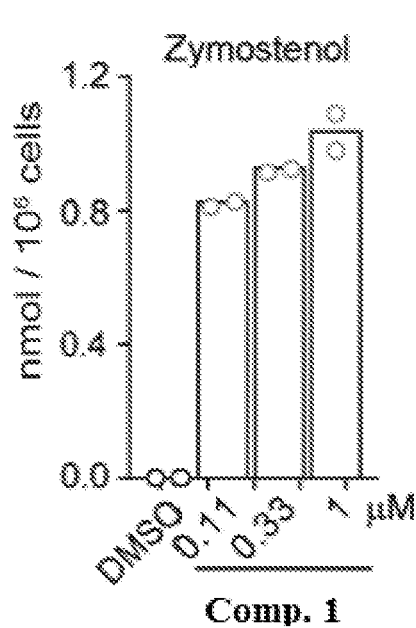
FIG. 3f illustrates GC-MS-based quantification of zymostenol, in OPC-5 after treatment with Compound 1.
Figure 3G:
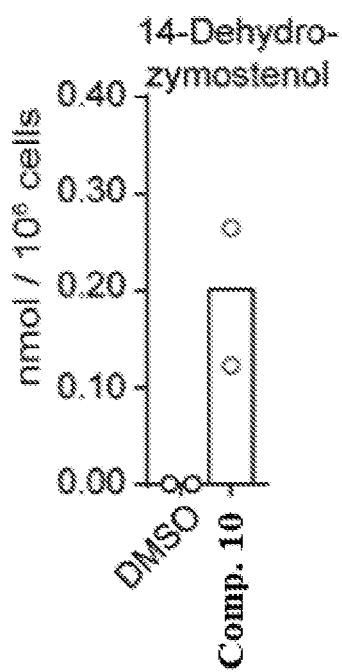
FIG. 3g illustrates GC-MS-based quantification of 14-dehydrozymostenol, in OPC-5 after treatment with Compound 10.
Figure 3H:
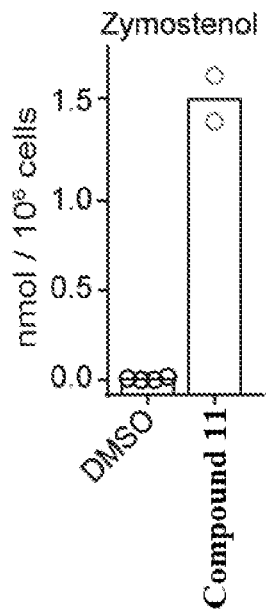
FIG. 3h illustrates GC-MS-based quantification of zymostenol, in OPC-5 after treatment with Compound 11. n=2 replicates per condition. Each analog was tested at 1 μM unless otherwise noted.

Next, selected analogs were evaluated for their effects on cholesterol biosynthesis using GC-MS-based sterol profiling in OPCs. First, the analogs that most potently enhanced oligodendrocyte formation were assayed at a uniform concentration of 1 µM. All the eight analogs were found to inhibit cholesterol biosynthesis and accumulate 8,9-unsaturated sterols (FIGS. 3a-3c, 3d-3e). Seven of the eight small molecules were found to accumulate zymostenol, indicative of EBP inhibition (FIGS. 3a-3c, 3f and 3h). OPCs treated with Compound 10 instead accumulated 14-dehydrozymostenol, indicative of inhibition of the upstream enzyme TM7SF2 (FIG. 3g).

Figure 4A:
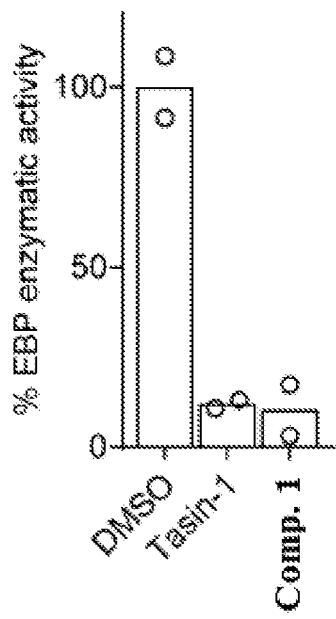
FIG. 4a illustrates EBP enzymatic activity in a biochemical assay at 10 μM. n=2 replicates per condition, representative of two independent experiments.
Figure 4B:
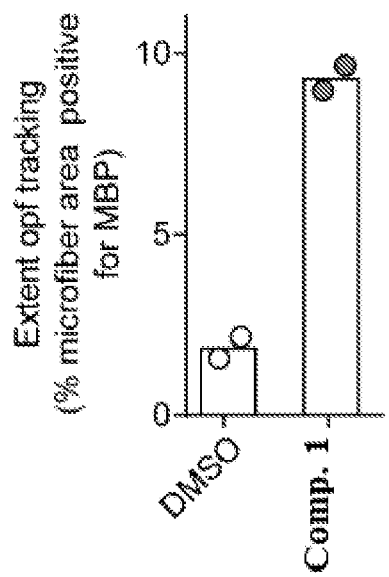
FIG. 4b illustrates quantification of the area of electrospun microfibers wrapped by MBP+ oligodendrocytes. n=2 wells per condition.
Figure 4C:
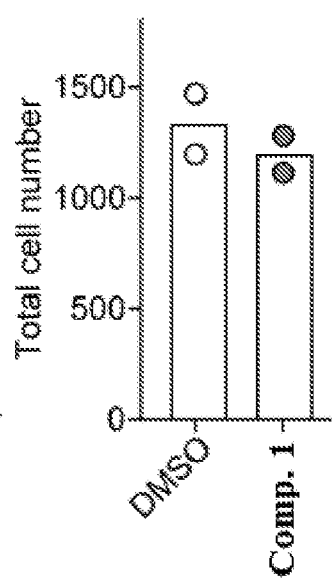
FIG. 4c illustrates total DAPI+ cell number for the experiment illustrated in FIG. 4b.
Figure 4D:
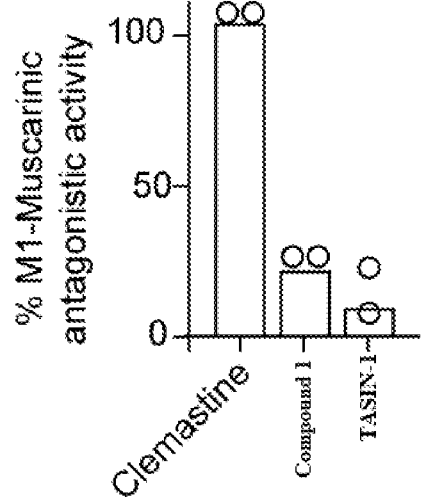
FIG. 4d illustrates inhibition of muscarinic receptor M1 by TASIN-1 (100 nM) and Compound 1 at 1 μM assayed using GeneBLAzer NFAT-bla CHO-K1 reporter cells, n=2 replicated per condition.
Figure 4E:
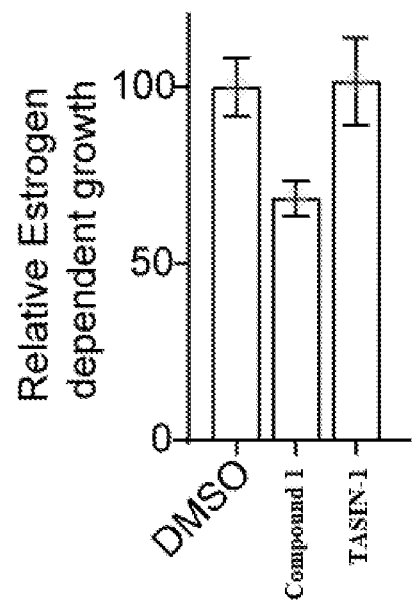
FIG. 4e illustrates effects of TASIN-1 (100 nM), and Compound 1 at 1 μM on the estrogen dependent growth of T47D cells, n=8 replicates per condition.
Figure 4F:
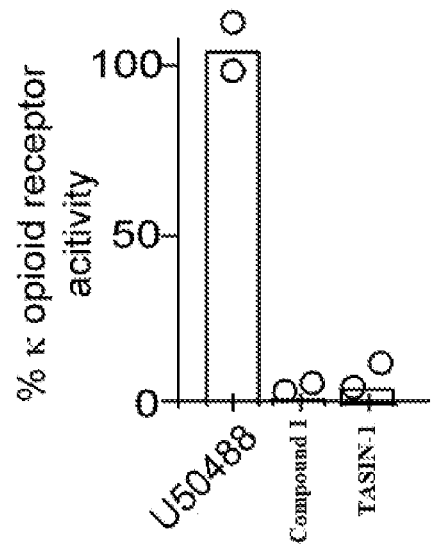
FIG. 4f illustrates activation of k-opioid receptor (OPRD1) by U50488 (2 μM), TASIN-1 (100 nM) and Compound 1 at 1 μM assayed using TangoOPRD1-bla U2OS reporter cells, n=2 replicated per condition. DMSO treatment condition was normalized to 0% and the activator U50488 treatment was normalized to 100%.
Figure 4G:
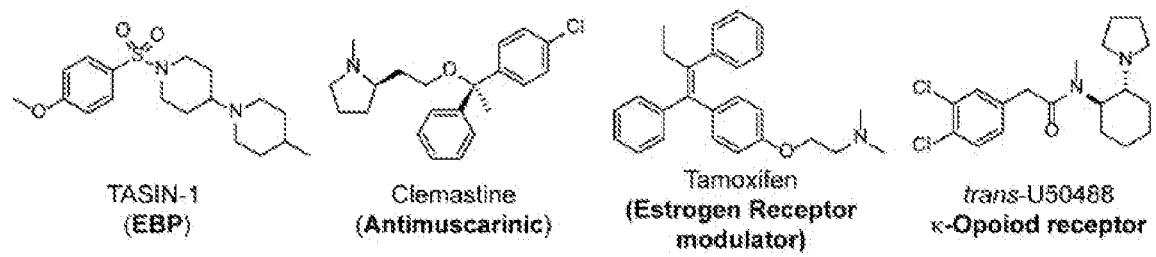
FIG. 4g illustrates structures and canonical targets of molecules that can inhibit EBP.
Figure 5:
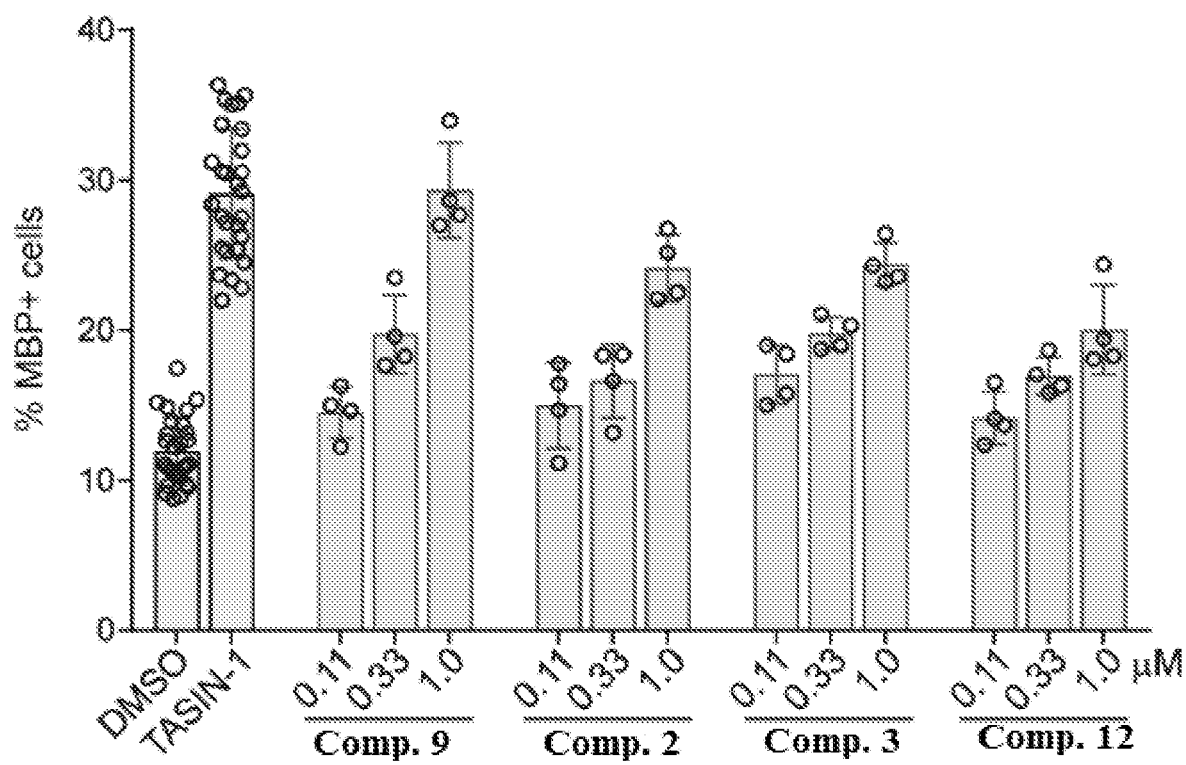
FIG. 5 illustrates percentage of MBP+ oligodendrocytes generated in OPC-5 after treatment with the indicated concentrations of small molecules for 72 h.

The inventors further characterized the most potent analog tested, Compound 1, which retained near maximal effects on oligodendrocyte formation at 110 nM, the lowest dose tested (FIG. 2a). GS-MS based sterol profiling of OPCs treated with a range of doses of Compound 1 confirmed that the enhanced potency for enhanced oligodendrocyte formation was matched by enhanced potency for EBP inhibition in OPCs (FIG. 3f) and in an in vitro enzymatic assay (FIG. 4a). Additionally, the inventors assessed whether the optimized enhancer of oligodendrocyte formation Compound 1 could also promote in vitro 'myelination', a necessary function for a pro-myelinating therapy. OPCs cultured on inorganic electrospun microfibers were treated with Compound 1 and the tracking of MBP+ oligodendrocytes along these axon-like substrates was quantified. Compound 1 treatment substantially increased the area of microfibers wrapped by MBP+ oligodendrocytes, indicating that Compound 1 treatment both enhances MBP+ oligodendrocyte formation and subsequent myelination in vitro (FIGS. 4b and 4c). These data support Compound 1 as a highly potent, cell-active enhancer of oligodendrocyte formation that functions by EBP inhibition. Additionally, across this set of analogs, the ability to inhibit EBP tracks closely with enhanced formation of oligodendrocytes, providing additional evidence supporting EBP as a target for enhancing oligodendrocyte formation and remyelination.

Finally, the small molecules identified previously that function in OPCs by inhibition of EBP, including clemastine, tamoxifen and U50488, have liabilities associated with modulation of these molecules' canonical targets that may limit their drug development potential. Hence, the leading novel EBP inhibitors identified in our screen as well as a previously characterized EBP inhibitor, TASIN-1, were tested in established cell-based assays for the M1 muscarinic receptor (clemastine), the estrogen receptor (tamoxifen), and the kappa opioid receptor (U50488). Each small molecule was tested at a concentration maximally effective for enhancing oligodendrocyte formation. While clemastine, tamoxifen, and U50488 were highly effective in assays for their respective targets, CW3388, and TASINI showed little affinity for any of these receptors (FIGS. 4d, 4e, 4f and 4g). Although these compounds, and TASINI may have cellular targets beyond EBP, these molecules lack the well-established and highly potent off-target effects common to other EBP-inhibiting scaffolds identified in drug repurposing screens, which may be beneficial in future medicinal chemistry studies aimed at further optimization of these scaffolds.

Discussion

Multiple diseases of the CNS, including multiple sclerosis, may benefit from new therapies that promote myelin repair. The inventors' recent work identified a unifying mechanism of action-inhibition of CYP51, TM7SF2, or EBP and subsequent accumulation of 8,9-unsaturated sterol intermediates-common to more than two dozen molecules identified as enhancing oligodendrocyte formation in drug repurposing screens. Here the inventors have used highthroughput screening of a large, structurally-diverse chemical library to corroborate and significantly extend our previous results. First, elucidation of the targets of our screening hits revealed that the majority enhanced oligodendrocyte formation by inhibiting CYP51, TM7SF2 or EBP and accumulated 8,9-unsaturated sterols, in line with results from past repurposing screens. However, several validated hits do not appear to affect cholesterol biosynthesis in OPCs, providing an opportunity to elucidate druggable mechanisms other than 8,9-unsaturated sterol accumulation for enhancing oligodendrocyte formation.

The studies described herein revealed a broad correlation between EBP inhibition and enhanced oligodendrocyte formation, providing further evidence supporting EBP as the functional target for this lead series. Finally, this approach identified an optimized EBP-inhibiting small molecule, Compound 1, that potently enhances oligodendrocyte formation and lacks potent off-target effects common to other molecules identified in repurposing efforts (FIGS. 4a, 4b, 4c, 4d, 4e and 4f). Overall, these findings further support inhibition of CYP51, TM7SF2, and in particular EBP as a central mechanism for many small molecule enhancers of oligodendrocyte formation and also define a novel N-benzylpiperidine-based series of potent, selective EBP inhibitors for further optimization toward remyelinating therapeutics.

Methods

Small Molecules

Many compounds falling within the scope of Formulas (I) and (II) can be obtained from commercial sources. Alternatively, compounds of Formula (I) can be obtained by reductive amination of the appropriate benzaldehyde aralkylaldehyde with the appropriate cyclic amine, as shown in Scheme 1 below:

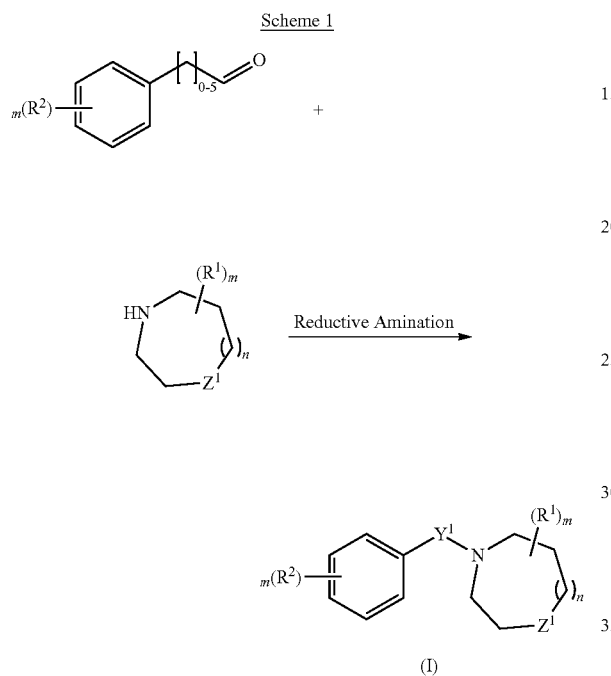

Suitable conditions for reductive amination are well known in the art and are described, for example, in Long et al., *J. Med. Chem.* 53:1830 (2010) and Abdel-Magid et al., *J. Org. Chem.*, 61:3849 (1996). Depending on the value of $R^1$, $R^2$ and $Z^1$, it may be necessary to utilize protecting groups during the reductive amination. The use of protecting groups is also well known in the art and is described, for example, in Protecting Groups in Organic Synthesis, T. W. Greene and P. G. M. Wuts, $3^{rd}$ edition, John Wiley & Sons, 1999.

Alternatively, compounds of Formula (II) can be obtained from O-benzyl tyrosines, as shown in Scheme 2 below:

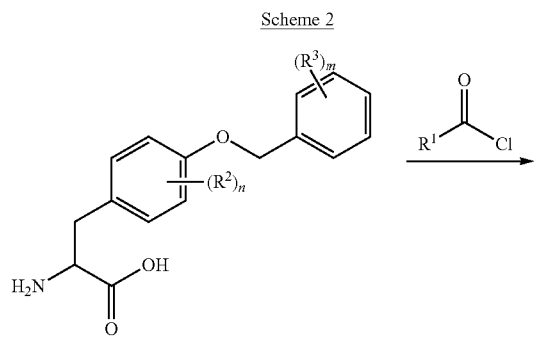

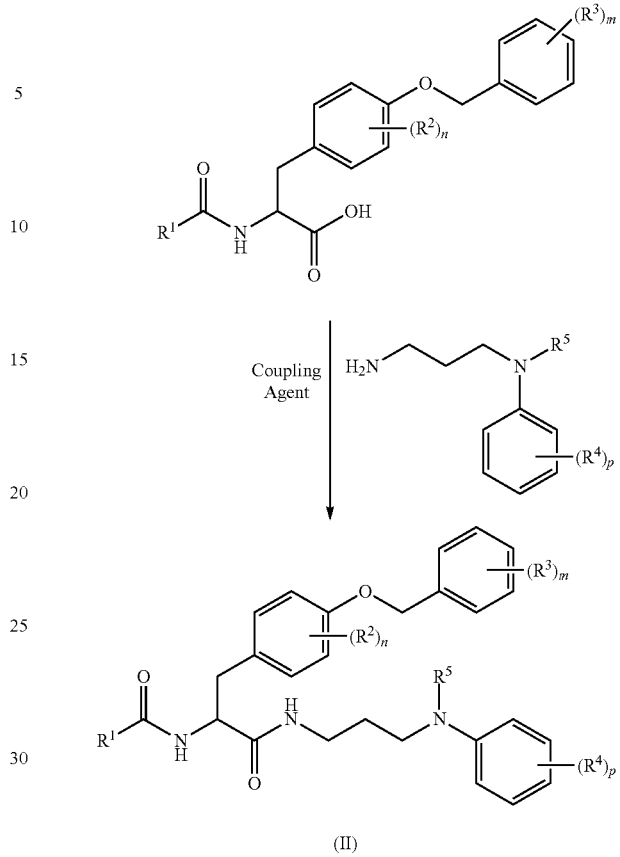

O-Benzyl tyrosines are commercially available from, for example, Aldrich Chemical Co., or can be readily prepared by persons of ordinary skill in the art. Acylation of the amine group of O-benzyl tyrosines can be carried out by routine procedures disclosed, for example, in Zabicky "The Chemistry of Amides" pages 73-185, Interscience, New York, 1970 and Baldwin et al., *J. Org. Chem.*, 30:671 (1965). Amide formation can be accomplished via coupling agents, such as dicyclohexylcarbodiimide, as described in Albertson and Klausner *Org. React* 12:157 (1962) and Bodansky *Synthesis* 1972:453 (1972). Protecting groups can be used, as appropriate.

The identity and purity of small molecules were authenticated by LC-MS before use. Ketoconazole and U50488 were purchased from Sigma-Aldrich as solid. The following compounds were purchased from Cayman Chemicals as solids: liothyronine, clemastine and Ro-48-8071. Amorolfine was purchased from Selleck Chemicals as 10 mM DMSO solution. TASIN-1 was synthesized as reported.

Mouse OPC Preparation

To rigorously assess effects of small molecule and genetic treatments on OPCs, all treatments were assayed in two batches of epiblast stem cell-derived OPCs, and key results were confirmed using mouse primary OPCs. OPCs were generated from two separate EpiSC lines, EpiSC5 (giving rise to OPC-5 OPCs) and 12901 (giving rise to OPC-1 OPCs). EpiSC-derived OPCs were obtained using in vitro differentiation protocols and culture conditions described previously. To ensure uniformity throughout all in vitro screening experiments, EpiSC-derived OPCs were sorted to purity by fluorescence activated cell sorting at passage five with conjugated CD 140a-APC (eBioscience, 17-1401;

1:80) and NG2-AF488 (Millipore, AB5320A4; 1:100) antibodies. Sorted batches of OPCs were expanded and frozen down in aliquots. OPCs were thawed into growth conditions for one passage before use in further assays. Cultures were regularly tested and shown to be *mycoplasma* free.

In Vitro Phenotypic Screening of OPCs

EpiSC-derived OPCs were grown and expanded in poly-ornithine (PO) and laminin-coated flasks with growth medium (DMEM/F12 supplemented with N2-MAX (R&D Systems), B-27 (ThermoFisher), GlutaMax (Gibco), FGF2 (10 µg/mL, R&D systems, 233-FB-025) and PDGF-AA (10 µg/mL, R&D systems, 233-AA-050) before harvesting for plating. The cells were seeded onto poly-D-lysine 96-well CellCarrier or CellCarrierUltra plates (PerkinElmer) coated with laminin (Sigma, L2020; 15 µg/ml) using multi-channel pipet. For the experiment, 800,000 cells/mL stock in differentiation medium (DMEM/F12 supplemented with N2-MAX and B-27) was prepared and stored on ice for 2 h. Then, 40,000 cells were seeded per well in differentiation medium and allowed to attach for 30 min before addition of drug. For dose-response testing of all molecules except sterols, a 1000× compound stock in dimethyl sulphoxide (DMSO) was added to assay plates with 0.1 µL solid pin multi-blot replicators (V & P Scientific; VP 409), resulting in a final primary screening concentration of 1×. Cells were incubated under standard conditions (37° C., 5% CO2) for 3 days and fixed with 4% paraformaldehyde (PFA) in phosphate buffered saline (PBS) for 20 min. Fixed plates were washed with PBS (200 µL per well) twice, permeabilized with 0.1% Triton X-100 and blocked with 10% donkey serum (v/v) in PBS for 40 min. Then, cells were labelled with MBP antibodies (Abcam, ab7349; 1:200) for 16 h at 4° C. followed by detection with Alexa Fluor conjugated secondary antibodies (1:500) for 45 min. Nuclei were visualized by DAPI staining (Sigma; 1 µg/ml). During washing steps, PBS was added using a multi-channel pipet and aspiration was performed using Biotek EL406 washer dispenser (Biotek) equipped with a 96-well aspiration manifold.

High-Content Imaging and Analysis

Plates were imaged on the Operetta High Content Imaging and Analysis system (PerkinElmer) and a set of 6 fields captured from each well resulting in an average of 1200 cells being scored per well. Analysis (PerkinElmer Harmony and Columbus software) began by identifying intact nuclei stained by DAPI; that is, those traced nuclei that were larger than 300 µm2 in surface area. Each traced nucleus region was then expanded by 50% and cross-referenced with the mature myelin protein (MBP) stain to identify oligodendrocyte nuclei, and from this the percentage of oligodendrocytes was calculated.

High-Throughput Screening of 10,000 Bioactive Small Molecules

EpiSC-derived OPCs were grown and expanded in poly-ornithine and laminin-coated flasks before harvesting for plating. Cells were dispensed in differentiation media supplemented with Noggin (R&D Systems; 100 ng/ml), Neurotrophin 3 (R&D Systems; 10 ng/ml), cAMP (Sigma; 50 µM), and IGF-1 (R&D Systems; 100 ng/ml)) using a Biotek EL406 Microplate Washer Dispenser (Biotek) equipped with 5 µL dispense cassette (Biotek), into poly-D-lysine/laminin (Sigma, L2020; 4 µg/ml)-coated sterile, 384-well, CellCarrier ultra plates (PerkinElmer), to a final density of 12,500 cells per well and allowed to attach for 45 min before addition of drug. A 10 mM stock of diverse 10,000 small molecules library in dimethylsulphoxide (DMSO) were prepared in an Abgene storage 384-well plate (ThermoFisher Scientific; AB1055). These were added to assay plates using a 50 nL solid pin tool attached to Janus automated workstation (Perkin Elmer), resulting in a final screening concentration of 10 µM. After incubation at 37° C. for 72 h, cells were fixed, washed and stained similar to 96-well OPC assay protocol, although all the washing steps were performed using a Biotek EL406 Microplate Washer Dispenser (Biotek) equipped with a 96-well aspiration manifold. Cells were stained with DAPI (Sigma; 1 µg/ml) and MBP antibody (Abcam, ab7349; 1:100). Plates were imaged on the Operetta High Content Imaging and Analysis system (PerkinElmer) and a set of 4 fields captured from each well resulting in an average of 700 cells being scored per well. Analysis was performed as in High-Content Imaging and Analysis, above. All plates for the primary screen were processed and analyzed simultaneously to minimize variability. Molecules causing more than 20% reduction in nuclear count relative to DMSO control wells were removed from consideration, and hits were called on the basis of largest fold-increase in percentage of MBP+ oligodendrocytes relative to DMSO controls within the same plate.

GC/MS-Based Sterol Profiling

EpiSC-derived OPCs were plated at 0.5 million cells per ml in PDL- and laminin-coated six or twelve well plate with differentiation media. After 24 hours, cells were dissociated with Accutase, rinsed with saline, and cell pellets were frozen. For sterol analyses, cells were lysed in methanol (Sigma-Aldrich) with agitation for 30 minutes and cell debris removed by centrifugation at 10,000 rpm for 15 min. Cholesterol-d7 standard $(25,26,26,26,27,27,27-^2H_7$-cholesterol, Cambridge Isotope Laboratories) was added before drying under nitrogen stream and derivatization with 55 µl of bis(trimethylsilyl)trifluoroacetamide/trimethylchlorosilane to form trimethylsilyl derivatives. Following derivatization at 60° C. for 20 minutes, 1 µl was analyzed by gas chromatography/mass spectrometry using an Agilent 5973 Network Mass Selective Detector equipped with a 6890 gas chromatograph system and a HP-5MS capillary column (60 m×0.25 mm×0.25 m). Samples were injected in splitless mode and analyzed using electron impact ionization. Ion fragment peaks were integrated to calculate sterol abundance, and quantitation was relative to cholesterol-d7. The following m/z ion fragments were used to quantitate each metabolite: cholesterol-d7 (465), FF-Mas (482), cholesterol (368), zymostenol (458), zymosterol (456), desmosterol (456, 343), 7-dehydrocholesterol (456, 325), lanosterol (393), lathosterol (458), 14-dehydrozymostenol (456). Calibration curves were generated by injecting varying concentrations of sterol standards and maintaining a fixed amount of cholesterol-D7. The human glioma cell line GBM528 was a gift of Jeremy Rich (Cleveland Clinic). Human cortical spheroids were generated as described previously.

EBP Enzymatic Assay

EBP enzymatic activity was measured using a reported method with slight modifications: active EBP was obtained from mouse microsomes, inhibitors were added, zymostenol was added at a final concentration of 25 µM in a final reaction volume of 500 µl, and the reaction incubated at 37° C. for 2 h. Sterols were extracted using 3×1 ml hexanes, cholesterol-d7 was added to enable quantitation, and the pooled organics were dried (Na2SO4) and evaporated under nitrogen gas. Samples were then silylated and analyzed using GC/MS as described above.

Estrogen-Dependent Cell Proliferation Assay

Estrogen-dependent cell proliferation was measured as previously described with minor modifications. After growth in estrogen-free media (Phenol red-free RPMI supplemented with 10% charcoal stripped fetal bovine serum) for 5 days, cells were seeded at 2,500 cells/well into 96 well plates. The following day 3× drug containing media was added to triplicate wells and cells were allowed to grow for an additional 5 days at 37° C. in standard a 5% $CO_2$ humidified incubator. Total DNA per well was measured using an adaptation of the method of Labarca and Paigen. At this time media was removed, cells were washed one time with 0.25×PBS and 100 µl of distilled water was added. Plates were frozen and thawed to enhance cell lysis and 200 µl of 10 µg/ml Hoechst 33258 (Sigma-Aldrich, St. Louis, MO) in 2M NaCl, 1 mM EDTA, 10 mM Tris-HCl pH 7.4 was added. After incubation at room temperature for 2 hours, plates were read in a SpectraMax i3 fluorescent plate reader (Molecular Devices, Sunnyvale, CA) with excitation at 360 nm and emission at 460 nm. All values were converted to microgram DNA per well using a standard curve derived from purified salmon testes DNA.

Muscarinic Receptor Antagonism Assay

GeneBLAzer M1-NFAT-bla CHO-K1 cells (or M3- or M5-NFAT-bla CHO-K1 cells)(ThermoFisher) were thawed into Assay Media (DMEM, 10% dialyzed FBS, 25 mM HEPES pH 7.3, 0.1 mM NEAA). 10,000 cells/well were added to a 384-well TC treated assay plate and incubated 16-24 h at 37° C. 4 µl of a 10× stock of antimuscarinic molecules was added to the plate and incubated 30 min. 4 µl of 10× control agonist Carbachol at the pre-determined EC80 concentration was added to wells containing antimuscarinic molecules. The plate was incubated 5 h and 8 µl of 1 µM Substrate+Solution D Loading Solution was added to each well and the plate was incubated 2 h at room temperature before reading on a fluorescence plate reader.

k-Opioid Receptor Agonism Assay

Tango-bla U2OS cells OPRD1 (ThermoFisher) were thawed into Assay Media (DMEM, 10% dialysed FBS, 25 mM HEPES pH 7.3, 0.1 mM NEAA). 10,000 cells/well were added to a 384-well TC treated assay plate. 8 µl of a 5× stock of test molecules or agonist (U50488) were added to the plate and incubated 16 h at 37° C. The plate was added with 8 µl of 1 µM substrate+solution D loading solution was added to each well and the plate was incubated 2 h in dark at room temperature before reading on a fluorescence plate reader. This cell line was validated in each run on the basis of z'>0.5 for agonist U50488 versus control treatment.

Oligodendrocyte Formation and Imaging on Electrospun Microfibers

A 12-well plate containing Mimetex aligned scaffold (microfiber plate, AMSBIO, AMS.TECL-006-1X, Electrospun poly-L-lactide Scaffold, 2 µM fibre diameter cell crown inserts) was prepared as previously described. Briefly, fiber inserts were sterilized with 70% ethanol and washed with PBS before being coated with polyornithine and laminin. After laminin coating, 100,000 cells/mL of EpiSC derived OPCs (1.5 mL/well) were plated in differentiation medium. After 24 h the media was replaced with fresh media containing small molecule treatments. Every 48 h the media was replaced with fresh compound containing media for the first 4 days of 14 days culture. Microfibre inserts were fixed with 4% PFA, permeabilized with 0.1% Triton X-100, and blocked with 10% donkey serum (v/v) in PBS for 60 min. Then stained for MBP (Abcam, ab7349; 1:100) and DAPI staining (Sigma; 5 µg/ml). After staining, the fiber inserts were mounted on a glass slide (Fisherbrand Superfrost Plus Microscope Slides) using Fluormount-G (Southern Biotech) with a cover glass (Fisherbrand Microscope Cover Glass) and dried at RT in dark for 36 h. The mounted inserts were imaged on the Operetta High Content Imaging and Analysis system (PerkinElmer) and a set of 22 fields captured from each condition resulting in an average of 2000 cells being scored per well. The total microfiber area was calculated using bright filed imaging and a spot finding function (area larger than 2 px2). The MBP+ pixel area within the defined microfiber area was then defined and the percentage of the total microfiber area calculated.

The entire content of each reference is hereby incorporated herein by reference.

REFERENCES

1. Bechler, M. E., Byrne, L. & Ffrench-Constant, C. CNS Myelin Sheath Lengths Are an Intrinsic Property of Oligodendrocytes. *Curr. Biol.* 25, 2411-2416, doi: 10.1016/j.cub.2015.07.056 (2015).
2. Lassmann, H. Classification of demyelinating diseases at the interface between etiology and pathogenesis. *Curr. Opin. Neurol.* 14, 253-258 (2001).
3. Fancy, S. P. et al. Overcoming remyelination failure in multiple sclerosis and other myelin disorders. *Exp. Neurol.* 225, 18-23, doi:10.1016/j.expneurol.2009.12.020 (2010).
4. Keirstead, H. S. & Blakemore, W. F. The role of oligodendrocytes and oligodendrocyte progenitors in CNS remyelination. *Adv. Exp. Med. Biol.* 468, 183-197 (1999).
5. Franklin, R. J. & Ffrench-Constant, C. Remyelination in the CNS: from biology to therapy. *Nat. Rev. Neurosci.* 9, 839-855, doi:10.1038/nrn2480 (2008).
6. Hubler, Z. et al. Accumulation of 8,9-unsaturated sterols drives oligodendrocyte formation and remyelination. *Nature* In Press, doi:10.1038/s41586-018-0360-3 (2018).
7. Najm, F. J. et al. Drug-based modulation of endogenous stem cells promotes functional remyelination in vivo. *Nature* 522, 216-220, doi:10.1038/nature14335 (2015).
8. Deshmukh, V. A. et al. A regenerative approach to the treatment of multiple sclerosis. *Nature* 502, 327-332, doi:10.1038/nature12647 (2013).
9. Mei, F. et al. Micropillar arrays as a high-throughput screening platform for therapeutics in multiple sclerosis. *Nat. Med.* 20, 954-960, doi:10.1038/nm.3618 (2014).
10. Mei, F. & Mayoral, S. R. Identification of the Kappa-Opioid Receptor as a Therapeutic Target for Oligodendrocyte Remyelination. *J. Neurosci.* 36, 7925-7935, doi: 10.1523/jneurosci.1493-16.2016 (2016).
11. Huang, J. K. et al. Retinoid X receptor gamma signaling accelerates CNS remyelination. *Nat. Neurosci.* 14, 45-53, doi:10.1038/nn.2702 (2011).
12. Gonzalez, G. A. et al. Tamoxifen accelerates the repair of demyelinated lesions in the central nervous system. *Sci. Rep.* 6, 31599, doi:10.1038/srep31599 (2016).
13. Lariosa-Willingham, K. D. et al. A high throughput drug screening assay to identify compounds that promote oligodendrocyte differentiation using acutely dissociated and purified oligodendrocyte precursor cells. *BMC. Res. Notes* 9, 419, doi:10.1186/s13104-016-2220-2 (2016).
14. Korade, Z. et al. The Effect of Small Molecules on Sterol Homeostasis: Measuring 7-Dehydrocholesterol in Dhcr7-Deficient Neuro2a Cells and Human Fibroblasts. *J. Med. Chem.* 59, 1102-1115, doi:10.1021/acs.jmedchem.5b01696 (2016).
15. Giera, M., Muller, C. & Bracher, F. Analysis and Experimental Inhibition of Distal Cholesterol Biosynthesis. *Chromatographia* 78, 343-358, doi:10.1007/s10337-014-2796-4 (2015).

16. Kubo, N., Shirakawa, O., Kuno, T. & Tanaka, C. Antimuscarinic effects of antihistamines: quantitative evaluation by receptor-binding assay. *Jpn. J. Pharmacol.* 43, 277-282 (1987).
17. Horwitz, K. B., Koseki, Y. & McGuire, W. L. Estrogen control of progesterone receptor in human breast cancer: role of estradiol and antiestrogen. *Endocrinology* 103, 1742-1751, doi:10.1210/endo-103-5-1742 (1978).
18. Von Voigtlander, P. F. & Lewis, R. A. U-50,488, a selective kappa opioid agonist: comparison to other reputed kappa agonists. *Prog. Neuropsychopharmacol. Biol. Psychiatry* 6, 467-470 (1982).
19. Najm, F. J. et al. Rapid and robust generation of functional oligodendrocyte progenitor cells from epiblast stem cells. *Nat Methods* 8, 957-962, doi:10.1038/nmeth.1712.
20. Pasca, A. M. et al. Functional cortical neurons and astrocytes from human pluripotent stem cells in 3D culture. *Nat Methods* 12, 671-678, doi:10.1038/nmeth.3415 (2015).
21. Moebius, F. F. et al. Pharmacological analysis of sterol delta8-delta7 isomerase proteins with [3H]ifenprodil. *Mol Pharmacol* 54, 591-598 (1998).
22. Pink, J. J. & Jordan, V. C. Models of estrogen receptor regulation by estrogens and antiestrogens in breast cancer cell lines. *Cancer Res* 56, 2321-2330 (1996).
23. Labarca, C. & Paigen, K. A simple, rapid, and sensitive DNA assay procedure. *Anal Biochem* 102, 344-352 (1980)

The invention claimed is:

1. A pharmaceutical composition comprising a pharmaceutically effective amount of a compound or a pharmaceutically acceptable salt thereof, and a pharmaceutically acceptable carrier or diluent, wherein the compound is represented by the following formula:

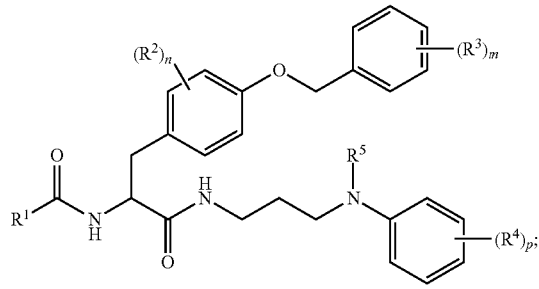

wherein:
$R^1$ is H, alkyl optionally substituted with hydroxyl, alkoxy, thiol, alkylthiol, halo, cyano, or phenyl, wherein the phenyl is optionally substituted with halo, alkoxyl, haloalkoxy, alkyl, haloalkyl, or cyano, or phenyl optionally substituted with halo, alkoxyl, haloalkoxy, alkyl, haloalkyl, or cyano, each $R^2$, $R^3$ and $R^4$ is independently halo, alkoxyl, haloalkoxy, alkyl, haloalkyl or cyano;
$R^5$ is H or alkyl; and
m, n or p are independently 0, 1 or 2.

2. The pharmaceutical composition of claim 1, where the compound is represented by the following structural formula:

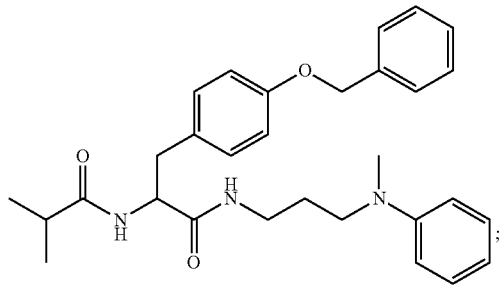 [SMILES: CC(C)C(=O)NC(Cc1ccc(OCc2ccccc2)cc1)C(=O)NCCCN(C)c1ccccc1]

3. The pharmaceutical composition of claim 1, wherein $R^5$ is $C_1$-$C_2$ alkyl.

4. A method of promoting myelination in a subject in need thereof, the method comprising administering to the subject an effective amount of the pharmaceutical composition of claim 1 or the compound recited in claim 1 or a pharmaceutically acceptable salt thereof.

5. A method of treating a myelin related disorder in a subject, the method comprising administering to the subject of the pharmaceutical composition of claim 1 or the compound recited in claim 1 or a pharmaceutically acceptable salt thereof.

6. The method of claim 5, wherein the myelin related disorder is multiple sclerosis (MS), neuromyelisits optica (NMO), progressive multifocal leukoencephalopathy (PML), encephalomyelitis (EPL), central pontine myelolysis (CPM), adrenoleukodystrophy, Alexander's disease, Pelizaeus Merzbacher disease (PMD), Vanishing White Matter Disease, Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, Bassen-Kornzweig syndrome, Marchiafava-Bignami syndrome, metachromatic leukodystrophy, trigeminal neuralgia, acute dissmeminated encephalitis, Guillian-Barre syndrome, Charcot-Marie-Tooth disease Bell's palsy, a mental health disorder, or schizophrenia.

7. The method of claim 6, wherein the multiple sclerosis is relapsing remitting multiple sclerosis, primary progressive multiple sclerosis or secondary progressive multiple sclerosis.

* * * * *